(12) United States Patent
Hu et al.

(10) Patent No.: US 7,498,417 B2
(45) Date of Patent: *Mar. 3, 2009

(54) ANTIBODIES TO VASCULAR ENDOTHELIAL GROWTH FACTOR 2 AND METHODS OF USING SAME

(75) Inventors: Jing-Shan Hu, Mountain View, CA (US); Craig A. Rosen, Laytonsville, MD (US); Liang Cao, Bethesda, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 361 days.

This patent is subject to a terminal disclaimer.

(21) Appl. No.: 10/853,232

(22) Filed: May 26, 2004

(65) Prior Publication Data

US 2004/0214286 A1 Oct. 28, 2004

Related U.S. Application Data

(60) Continuation of application No. 10/060,523, filed on Feb. 1, 2002, now abandoned, which is a continuation of application No. 09/618,451, filed on Jul. 18, 2000, now abandoned, which is a continuation of application No. 09/257,918, filed on Feb. 26, 1999, now abandoned, which is a division of application No. 08/824,996, filed on Mar. 27, 1997, now Pat. No. 5,935,820, which is a division of application No. 08/207,550, filed on Mar. 8, 1994, now abandoned.

(51) Int. Cl.
*C07K 16/00* (2006.01)
*A01N 37/18* (2006.01)
*A61K 38/00* (2006.01)

(52) U.S. Cl. .................. 530/387.1; 514/2
(58) Field of Classification Search .............. None
See application file for complete search history.

(56) References Cited

U.S. PATENT DOCUMENTS

| | | | |
|---|---|---|---|
| 5,073,492 A | 12/1991 | Chen et al. |
| 5,194,596 A | 3/1993 | Tischer et al. |
| 5,219,739 A | 6/1993 | Tischer et al. |
| 5,234,908 A | 8/1993 | Szabo et al. |
| 5,240,848 A | 8/1993 | Keck et al. |
| 5,283,354 A | 2/1994 | Lemischka |
| 5,326,695 A | 7/1994 | Andersson et al. |
| 5,607,918 A | 3/1997 | Eriksson et al. |
| 5,633,147 A | 5/1997 | Meissner et al. |
| 5,652,225 A | 7/1997 | Isner |
| 5,661,133 A | 8/1997 | Leiden et al. |
| 5,693,622 A | 12/1997 | Wolff et al. |
| 5,776,755 A | 7/1998 | Alitalo et al. |
| 5,792,453 A | 8/1998 | Hammond et al. |
| 5,840,693 A | 11/1998 | Eriksson et al. |
| 5,861,301 A | 1/1999 | Terman et al. |
| 5,932,540 A | 8/1999 | Hu et al. |
| 5,935,820 A | 8/1999 | Hu et al. |
| 6,040,157 A | 3/2000 | Hu et al. |
| 6,121,246 A | 9/2000 | Isner |
| 6,130,071 A | 10/2000 | Alitalo et al. |
| 6,221,839 B1 | 4/2001 | Alitalo et al. |
| 6,245,530 B1 | 6/2001 | Alitalo et al. |
| 6,361,946 B1 | 3/2002 | Alitalo et al. |
| 6,403,088 B1 | 6/2002 | Alitalo et al. |
| 6,451,764 B1 | 9/2002 | Lee et al. |
| 6,608,182 B1 | 8/2003 | Rosen et al. |
| 6,645,933 B1 | 11/2003 | Alitalo et al. |
| 6,734,285 B2 | 5/2004 | Hu et al. |
| 6,884,879 B1 | 4/2005 | Baca et al. |
| 7,109,308 B1 | 9/2006 | Rosen et al. |
| 7,115,392 B2 | 10/2006 | Rosen et al. |
| 7,153,827 B1 | 12/2006 | Hu et al. |
| 7,153,942 B2 | 12/2006 | Hu et al. |
| 7,186,688 B1 | 3/2007 | Hu et al. |
| 7,208,582 B2 | 4/2007 | Rosen et al. |
| 7,223,724 B1 | 5/2007 | Alderson et al. |
| 7,227,005 B1 | 6/2007 | Hu et al. |
| 7,273,751 B2 | 9/2007 | Coleman |
| 7,402,312 B2 | 7/2008 | Rosen et al. |
| 7,439,333 B2 | 10/2008 | Hu et al. |
| 2003/0215921 A1 | 11/2003 | Coleman |
| 2005/0059117 A1 | 3/2005 | Rosen et al. |
| 2005/0176103 A1 | 8/2005 | Hu et al. |
| 2005/0181979 A1 | 8/2005 | Alderson et al. |
| 2005/0192429 A1 | 9/2005 | Rosen et al. |
| 2005/0232921 A1 | 10/2005 | Rosen et al. |
| 2005/0287143 A1 | 12/2005 | Rosen et al. |
| 2006/0014252 A1 | 1/2006 | Lyman |
| 2006/0025331 A1 | 2/2006 | Hu et al. |
| 2006/0057117 A1 | 3/2006 | Coleman |

FOREIGN PATENT DOCUMENTS

AU 710696 9/1999

(Continued)

OTHER PUBLICATIONS

U.S. Appl. No. 11/980,495, inventors Rosen et al., filed Oct. 31, 2007 (not published).

(Continued)

*Primary Examiner*—Robert Landsman
(74) *Attorney, Agent, or Firm*—Sterne, Kessler, Goldstein & Fox P.L.L.C.

(57) ABSTRACT

Disclosed is a human VEGF2 polypeptide and DNA(RNA) encoding such VEGF2 polypeptides. Also provided is a procedure for producing such polypeptide by recombinant techniques and antibodies and antagonist against such polypeptide. Such polypeptides may be combined with a suitable pharmaceutical carrier or diluent to provide diagnostic, therapeutic and/or prophylactic effects against various diseases. Also provided are methods of using the antibodies and antagonists to inhibit the action of VEGF2 for therapeutic purposes.

18 Claims, 10 Drawing Sheets

FOREIGN PATENT DOCUMENTS

| | | |
|---|---|---|
| EP | 0186084 A2 | 7/1986 |
| EP | 0399816 A1 | 11/1990 |
| EP | 0476983 | 3/1992 |
| EP | 0506477 | 9/1992 |
| JP | 64-38100 A | 2/1989 |
| JP | 2-117698 A | 5/1990 |
| WO | WO 91/02058 | 2/1991 |
| WO | WO 92/14748 | 9/1992 |
| WO | WO 94/11506 A1 | 5/1994 |
| WO | WO 95/19985 | 7/1995 |
| WO | WO 95/24414 | 9/1995 |
| WO | WO 95/24473 | 12/1995 |
| WO | WO 96/05856 | 2/1996 |
| WO | WO 96/39515 | 12/1996 |
| WO | WO 97/00271 | 1/1997 |
| WO | WO 97/05250 | 2/1997 |
| WO | WO 97/08320 | 3/1997 |
| WO | WO 97/09427 | 3/1997 |
| WO | WO 97/17442 | 5/1997 |
| WO | WO 97/19694 | 6/1997 |
| WO | WO 98/06844 | 2/1998 |
| WO | WO 98/07832 | 2/1998 |
| WO | WO 98/24811 | 6/1998 |
| WO | WO 98/33917 | 6/1998 |
| WO | WO 98/39035 | 9/1998 |
| WO | WO 98/49300 | 11/1998 |
| WO | WO 98/55619 | 12/1998 |
| WO | WO 98/56936 | 12/1998 |
| WO | WO 99/02545 | 1/1999 |
| WO | WO 99/08522 | 2/1999 |
| WO | WO 99/20749 | 4/1999 |
| WO | WO 99/21590 | 5/1999 |
| WO | WO 99/46364 | 9/1999 |
| WO | WO 00/45835 A1 | 8/2000 |
| WO | WO 00/73430 | 12/2000 |
| WO | WO 00/75163 | 12/2000 |
| WO | WO 01/57226 A1 | 8/2001 |
| WO | WO 01/58956 | 8/2001 |
| WO | WO 02/11769 A1 | 2/2002 |
| WO | WO 02/083704 A1 | 10/2002 |
| WO | WO 02/083849 A2 | 10/2002 |
| WO | WO 02/083850 A2 | 10/2002 |
| WO | WO 03/097660 A1 | 11/2003 |
| ZA | 9-403464 | 1/1996 |

OTHER PUBLICATIONS

Achen et al., "Vascular endothelial growth factor D (VEGF-D) is a ligand for the tyrosine kinases VEGF receptor-2 (Flk1) and VEGF receptor 3 (Flt4)," *Proc. Natl. Acad. Sci. (USA) 95*:548-553, National Academy of Sciences (Jan. 1998).

Alderson et al., "Vascular endothelial cell growth factor (VEGF)-2 enhances the development of rat photoreceptor cells in vitro," *Keystone Symposia, Ocular Cell and Molec. Bio.* 202 (1999).

Altshuler et al., "Taurine promotes the differentiation of a vertebrate retinal cell type in vitro," *Development 119*:1317-1328, Company of Biologists Limited (Dec. 1993).

Andersson et al., "Assignment of interchain disulfide bonds in platelet-derived growth factor (PDGF) as evidence for agonist activity of monomeric PDGF," *J. Bio. Chem. 267*:11260-11266, American Society for Biochemistry and Molecular Biology (1992).

Andersson, W.F. "Human gene therapy," *Science 256*:808-813, American Association for the Advancement of Science (1992).

Aprelikova et al., "FLT4, a novel class III receptor tyrosine kinase in chromosome 5q33-qter," *Cancer Res. 52*:746-748, American Association for Cancer Research (1992).

Bell et al., "Human epidermal growth factor precursor: cDNA sequence, expression in vitro and gene organization," *Nucl. Acids Res. 14*:8427-8446, Oxford University Press (1986).

Bellomo et al., "Mice Lacking the Vascular Endothelial Growth Factor-B Gene (Vegfb) Have Smaller Hearts, Dysfunctional Coronary Vasculature, and Impaired Recovery From Cardiac Ishemia," *Circ. Research 86*:e29-e35, Lippincott, Williams & Wilkins (Feb. 2000).

Berse et al., "Vascular permeability factor (vacular endothelial growth factor) gene is expressed differentially in normal tissues, macrophages, and tumors," *Mol. Biol. Cell. 3*:211-220, American Society for Cell Biology (1992).

Betsholtz et al., "cDNA sequence and chromosomal localization of human platelet-derived growth factor A-chain and its expression in tumor cell lines," *Nature 320*:695-699, Macmillan Publishers (1986).

Bocker-Meffert et al., "Erythropoietin and VEGF Promote Neural Outgrowth from Retinal Explants in Postnatal Rats," *Invest. Ophthalmol. Vis. Sci. 43*:2021-2026, Association for Research in Vision and Ophthalmology (June 2002).

Breier et al., "Expression of vascular endothelial growth factor during embryonic angiogenesis and endothelial cell differentiation," *Development 114*:521-532 (1992).

Claffey et al., "Vascular endothelial growth factor," *J. Biol. Chem. 267*:16317-16322 (1992).

Cockerill et al., "Angiogenesis: Models and Modulators," *Intl. Rev. Cytology 159*:113-160 (1995).

Corson et al., "Fibrillin binds calcium and is coded by cDNAs that reveal a multidomain structure and alternatively spliced exons at the 5' end," *Genomics 17*:476-484 (Aug. 1993).

Dignam et al., "Balbiani ring 3 in chironomus tentans encodes a 185-kDa secretory protein which is synthesized throughout the fourth larval instar," *Gene 88*:133-140 (1990).

Eichmann et al., "Avian VEGF-C: cloning, embryonic expression pattern and stimulation of the differentiation of VEGFR2-expressing endothelial cell precursor," *Development 125*:743-752 (Feb. 1998).

Ferrara et al., "Molecular and biological properties of the vascular endothelial growth factor family of proteins," *Endocrine Rev. 13*:18-32 (1992).

Ferrara et al., "The vascular endothelial growth factor family of polypeptides," *J. Cell. Bio. 47*:211-218 (1991).

Finnerty et al., "Molecular cloning of murine FLT and FLT4," *Oncogene 8*:2293-2298 (Aug. 1993).

Friedman, T., "A brief history of gene therapy," *Nat. Genetics 2*:93-98 (1992).

Seigel, G.M., "The golden age of retinal cell culture," *Molec. Vis. 5*:4 (Apr. 1999).

Gamble et al., "Regulation of In Vitro Capillary TubeFormation by Anti-Integrin Anbodies," *J. Cell. Bio. 121*:931-943 (May 1993).

George et al., "Current Methods in Sequence Comparison and Analysis," *Macromolecular Seq. and Syn. Selected Meth—Application* (Alan R. Liss), pp. 127-149 (1988).

Gerhardinger et al., "Expression of Vascular Endothelial Growth Factor in the Human Retina and in Nonproliferative Diabetic Retinopathy," *Am. J. Pathol. 152*:1453-1462 (Jun. 1998).

Goldspiel et al., "Human Gene Therapy," *Clin. Pharm. 12*:488-505 (Jul. 1993).

Grimmond et al., "Cloning and Characterization of a Novel Human Gene Related to Vascular Endothelial Growth Factor," *Genome Res. 6*:124-131 (Feb. 1996).

Guzman et al., "Efficient gene transfer into myocardium by direct injection of adenovirus vectors," *Circ. Res. 73*:1202-1207 (Dec. 1993).

Hannink et al., "Deletions in the C-Terminal Coding Region of the v-sis Gene: Dimerization Is Required for Transformation," *Mol. Cell. Biol.* 1304-1314 (1986).

Hirai et al., "Expression of Vascular Endothelial Growth Factors (VEGF-A/VEGF-1 and VEGF-C/VEGF-2) in Postmenopausal Uterine Endometrial Carcinoma," *Gynecol. Oncol. 80*:181-188 (Feb. 2001).

Heldin et al., "Structure of platelet-derived growth factor: implications for functional properties," *Growth Factors 8*:245-252 (1993).

Hockel et al., "Therapeutic angiogenesis," *Arch. Surg. 128*:423-429 (Apr. 1993).

Hu et al., "A novel regulatory function of proteolytically cleaved VEGF-2 for vascular endothelial smooth muscle cells," *FASEB J. 11*:498-504 (May 1997).

Hyde et al., "Correction of the ion transport defect in cystic fibrosis transgenic mice by gene therapy," *Nature 362*:250-255 (Mar. 1993).

Joukov et al., "A novel vascular endothelial factor, VEGF-C, is a ligand for the Flt4 (VEGFR-3) and KDR (VEGFR-2) receptor tyrosine kinases," *EMBO J.* 15:290-298 (Jan. 1996).

Joukov et al., "Proteolytic processing regulates receptor specificity and activity of VEGF-C," *EMBO J.* 16:3898-3911 (Jul. 1997).

Kaipinen et al., "The related FLT4, FLT1 and KDR receptor tyrosine kinases show distinct expression patterns in human fetal endothelial cells," *J. Exp. Med.* 178:2077-2088 (Dec. 1993).

Kay et al., "In Vivo Gene Therapy of Hemophilia B: Sustained Partial Correction in Factor IX-Deficient Dogs," *Science* 262:117-119 (October 1993).

Keck et al., Vascular permeability factor, an endothelial cell mitogen related to PDGF, *Science* 246: 1309 (1989).

Kelley et al., "Regulation of a Proliferation and Photoreceptor Differentiation in Fetal Human Retinal Cell Cultures," *Invest. Ophthalmol. Vis. Sci.* 36:1280-1289 (Jun. 1995).

Kingsley, D. "The TGF-b superfamily: new members, new receptors, and new genetic tests of function in different organisms," *Genes & Dev.* 8:133-146 (Jan. 1994).

Kilodka et al., "Hepatic Gene Therapy: Efficient Retroviral-Mediated Gene Transfer into Rat Hepatocyes in Vivo," *Som. Cell Mol. Gen.* 19:491-497 (Sep. 1993).

Kukk et al., "VEGF-C receptor binding and pattern of expression with VEGFR-3 suggests a role in lymphatic vascular development," *Development* 122:3829-3837 (Dec. 1996).

Lee et al., "Vascular endothelial growth factor-related protein: a ligand and specific activator of the tyrosine kinase receptor Flt4," *Proc. Natl. Acad. Sci.* (USA) 93:1988-1992 (Mar. 1996).

Leung et al., "Vascular endothelial growth factor is a secreted angiogenic mitogen," *Science* 246:1306-1309 (1989).

Litwin et al., "Role of Cytokines in Endothelial Cell Functions," *Human Cytokines* 101-129 (Apr. 1995).

Maglione et al., "Isolation of a human placenta cDNA coding for a protein related to the vascular permeability factor," *Proc. Natl. Acad. Sci.* (USA) 88:9267-9271 (1991).

Maglione et al., "Two alternative mRNAs coding for the angiogenic factor, placenta growth factor (PlGF), are transcribed from a single gene of chromosome 14," *Oncogene* 8:925-931 (1993).

Massague, J. "The transforming growth factor-beta family," *Annu. Rev. Cell Biol.* 6:597-641 (1990).

Matthews et al., "A receptor tyrosine kinase cDNA isolated from a population of enriched primitive hematopoietic cells and exhibiting close genetic linkage to c-kit," *Proc. Natl. Acad. Sci.* (USA) 88:9026-9030 (1991).

Millauer et al., "Glioblastoma growth inhibited in vivo by a dominant-negative Flk-1 mutant," *Nature* 367:576-579 (Feb. 1994).

Millauer et al., "High affinity VEGF binding and developmental expression suggest FLK-1 as a major regulator of vasculogenesis and angiogenesis," *Cell* 72:835-846 (Mar. 1993).

NGO et al., "The Protein Folding Problem and Tertiary Structure Prediction," Kenneth Merz, Jr. and Scott LeGrand eds., Birkhauser, Boston, pp. 492-495 (1994).

Oltvai et al., "Bcl-2 heterodimerizes in vivo with a conserved homolog, bax, that accelerates programmed cell death," *Cell* 74:609-619 (Aug. 1993).

Pajusola et al., "FLT4 receptor tyrosine kinase contains seven immunoglobulin-like loops and is expressed in multiple human tissues and cell lines," *Cancer Res.* 52:5738-5743 (1992).

Pajusola et al., "Two human FLT4 receptor tyrosine kinase isoforms with distinct carboxy terminal tails are produced by alternative processing of primary transcripts," *Oncogene* 82931-2937 (Nov. 1993).

Paulsson et al., "The balbani ring 3 gene in chironomus tentans has a diverged repetitive structure split by many introns," *J. Mol. Biol.* 211:331-349 (1990).

Rudikoff et al., "Single amino acid substitution altering antigen-binding specificity," *Proc. Natl. Acad. Sci. USA* 79:1979-1983 (1982).

Schratzberger et al., "Reversal of experimental diabetic neuropathy by VEGF gene transfer," *J. Clin. Invest.* 107:1083-1092 (May 2001).

Schulz-Key et al., "Ciliary Neurotrophic Factor as a Transient Negative Regulator of Rod Development in Rat Retina," *Invest Ophthalmol. Vis. Sci.* 43:3099-3108 (Sep. 2002).

Shibuya et al., "Nucleotide sequence and expression of a novel human receptor-type tyrosine kinase gene (*flt*) closely related to the *fms* family," Oncogene 519-524 (1990).

Silins et al., "Analysis of the Promoter Region of the Human VEGF-Related Factor Gene," *Biochem. Biophys. Res. Comm.* 230:413-418 (Jan. 1997).

Stacker et al., "The Vascular Endothelial Growth Factor Family: Signalling for Vascular Development," *Growth Factors* 17:1-11 (1999).

Stewart et al., "Insulin delivery by somatic cell gene therapy," *J. Mol. Endocrin.* 11:335-341 (Dec. 1993).

Tanaka et al., "DNA sequence encoding the amino-terminal region of the human c-*src* protein: implications of sequence divergence amon *src*-type kinase oncogenes, " *Mol. Cell Biol.* 7:1978-1983 (1987).

Terman et al., "Identification of the new endothelial cell growth factor receptor tyrosine kinase," *Oncogene* 6:1677-1683 (1991).

Terman et al., "Identification of the kdr tyrosine kinase as a receptor for vascular endothelial cell growth factor," *Biochem. Biophys. Res. Commun.* 187:1579-1586 (1992).

Tischer et al., "Vascular endothelial growth factor: A new member of the platelet-derived growth factor gene family," *Biochem. Biophys. Res. Commun.* 165:1198-1206 (1989).

Tischer et al., "The Human Gene for Vascular Endothelial Growth Factor," *J. Biol. Chem.* 266:11947-11954 (1991).

Townson et al., "Characterization of the Murine VEGF-Related Factor Gene," *Biochem. Biophys. Res. Commun.* 220:922-928 (Mar. 1996).

Tsujimoto et al., "Analysis of the structure, transcripts, and protein products of bcl-2, the gene involved in human follicular lymphoma," *Proc. Natl. Acad. Sci.* (USA) 83:5214-5218 (1986).

Vale et al., "Percutaneous Electromechanical Mapping Demonstrates Efficacy of pVGI.1 (VEGF2) in an Animal Model of Chronic Myocardial Ischemia," *Circulation* 100:I.22 (Dec. 1999).

Vale et al., "Randomized, Single-Blind, Placebo-Controlled Pilot Study of Catheter-Based Myocardial Gene Transfer for Therapeutic Angiogenesis Using Left Ventricular Electromechanical Mapping in Patients with Chronic Myocardial Ischemia," *Circulation* 103:2138-2143 (May 2001).

Walsh et al., "Gene Therapy for Human Hemoglobinopathies," *PSEBM* 204: 289-300 (1993).

Williams, R.S. "Southwestern internal medicine conference: prospects for gene therapy of ischemic heart disease," *Am. J. Med. Sci.* 306:129-136 (Aug. 1993).

Yang et al., "Flk-1, a Receptor for Vascular Endothelial Growth Factor (VEGF), Is Expressed by Retinal Progenitor Cells," *J. Neurosci.* 16:6089-6099 (Oct. 1996).

Yourey et al., "Vascular Endothelial Cell Growth Factors Promote the In Vitro Development of Rat Photoreceptor Cells," *Molecul. Biol. Cell* 10:39a (1999) and 39th Ann. Mtg. Am. Soc. Cell Biol., Washington, DC (1999) (abstract 227).

Yourey et al., "Vascular Endothelial Growth Factors Promote the In Vitro Development of Rat Photoreceptor Cells," *J. Neurosci.* 20:6781-6788 (Sep. 2000).

GenBank Accession No. X68203, Aprelikova et al., "H.sapiens mRNA for FLT4, class III receptor tyrosine kinase," Nov. 30, 1993.

GenBank Accession No. M95200, Claffey et al., "Mouse vascular endothelial growth factor mRNA, complete cds," Apr. 27, 1993.

GenBank Accession No. M24160, Dignam et al., "C.tentans 185-kd secretory protein (sp185) mRNA, partial cds, clone pCt185," Apr. 26, 1993.

GenBank Accession No. M24276, Dignam et al., "C.tentans 140-kd secretory protein (sp140) mRNA, partial cds, clone pCt140.1," Apr. 26, 1993.

GenBank Accession No. M24277, Dignam et al., "C.tentans 140-kd secretory protein (sp140) mRNA, partial cds, clone pCt140.2," Apr. 26, 1993.

GenBank Accession No. D88689, Finnerty et al., "Mus musculus mRNA for flt-1, complete cds," Apr. 14, 2000.

GenBank Accession No. L07296, Finnerty et al., "Mus musculus receptor tyrosine kinase (FLT4) mRNA, complete cds," Aug. 9, 1993.

GenBank Accession No. X54936, Maglione et al., "H.sapiens mRNA for placenta growth factor (PlGF)," Nov. 12, 1991.

GenBank Accession No. S57152, Maglione et al., "Homo sapiens placenta growth factor 2 (PIGF-2) gene, partial cds," Mar. 5, 2001.
GenBank Accession No. X59397, Matthews et al., Mouse Flk-1 mRNA for a tyrosine kinase receptor, Nov. 6, 1991.
GenBank Accession No. X52263, Paulsson et al., "C.tentans balbiani ring 3 (BR3) gene," Dec. 18, 1992.
GenBank Accession No. M63971, Tischer et al., "Human vascular endothelial cell growth factor gene, exon 1," Aug. 1993.
GenBank Accession No. M63972, Tischer et al., "Human vascular endothelial cell growth factor gene, exon 2," Aug. 3, 1993.
GenBank Accession No. M63973, Tischer et al., "Human vascular endothelial cell growth factor gene, exon 3," Aug. 3, 1993.
GenBank Accession No. M63974, Tischer et al., "Human vascular endothelial cell growth factor gene, exon 4,"Aug. 3, 1993.
GenBank Accession No. M63975, Tischer et al., "Human vascular endothelial cell growth factor gene, exon 5," Aug. 3, 1993.
GenBank Accession No. M63976, Tischer et al., "Human vascular endothelial cell growth factor gene, exon 6," Aug. 3, 1993.
GenBank Accession No. M63977, Tischer et al., "Human vascular endothelial cell growth factor gene, exon 7," Aug. 3, 1993.
GenBank Accession No. M63978, Tischer et al., "Human vascular endothelial cell growth factor gene, exon 8," Aug. 3, 1993.
GenBank Accession No. M27281, Keck et al., "Human vascular permeability factor mRNA, complete cds," Aug. 3, 1993.
GenBank Accession No. X04571, Bell et al., "Human mRNA for kidney epidermal growth factor (EGF) precursor," Mar. 21, 1995.
GenBank Accession No. X63556, Corson et al., "H.sapiens mRNA for fibrillin," Feb. 17, 1997.
GenBank Accession No. L19896, Corson et al., "Human fibrillin (FBN1) gene, 5'end including alternative exons A, B, and C, and exon M," Nov. 8, 1994.
GenBank Accession No. L04947, Terman et al., "Homo sapiens (clones BT3.081.8, BT3.129.5 and BT4.169," Jan. 6, 1995.
GenBank Accession No. M16237, Tanaka et al., "Human c-src-1 proto-oncogene, exon 2," Jan. 13, 1995.
GenBank Accession No. M16243, Tanaka et al., "Human c-src-1 proto-oncogene, exon 3," Jan. 13, 1995.
GenBank Accession No. M16244, Tanaka et al., "Human c-src-1 proto-oncogene, exon 4," Jan. 13, 1995
GenBank Accession No. M16245, Tanaka et al., "Human c-src-1 proto-oncogene, exon 5," Jan. 13, 1995.
GenBank Accession No. K03212, Anderson et al., "Human c-src-1 proto-oncogene, exon 6," Jan. 13, 1995.
GenBank Accession No. K03213, Anderson et al., "Human c-src-1 proto-oncogene, exon 7," Jan. 13, 1995.
GenBank Accession No. K03214, Anderson et al., "Human c-src-1 proto-oncogene, exon 8," Jan. 13, 1995.
GenBank Accession No. K03215, Anderson et al., "Human c-src-1 proto-oncogene, exon 9," Jan. 13, 1995.
GenBank Accession No. K03216, Tanaka et al., "Human c-src-1 proto-oncogene, exon 10," Jan. 13, 1995.
GenBank Accession No. K03217, Tanaka et al., "Human c-src-1 proto-oncogene, exon 11," Jan. 13, 1995.
GenBank Accession No. K03218, Tanaka et al., "Human c-src-1 proto-oncogene, exon 12," Jan. 13, 1995.
GenBank Accession No. M13994, Tsujimoto et al., "Human B-cell leukemia/lymphoma 2 (bcl-2) proto-oncogene mRNA endocing bcl-2-alpha protein, complete cds" Oct. 31, 1994.
GenBank Accession No. M13995, Tsujimoto et al., "Human B-cell leukemia/lymphoma 2 (bcl-2) proto-oncogene mRNA endocing bcl-3-beta protein, complete cds" Oct. 31, 1994.
GenBank Accession No. L22473, Oltvai et al., "Human Bax alpha mRNA, complete cds," Dec. 15, 1993.
GenBank Accession No. L22474, Oltvai et al., "Human Bax beta mRNA, complete cds," Dec. 13, 1993.
GenBank Accession No. AJ000185, Achen et al., "Homo Sapiens mRNA for vascular endothelial growth factor-D," Feb. 11, 1998.
GenBank Accession No. S08167, Paulsson et al., "Balbiani ring 3 protein—midge (*Chironomus tentans*)," 1990.
International Search Report, Application No. PCT/US99/05021.
International Search Report, Application No. PCT/US94/05291.
International Search Report, Application No. PCT/US01/24658.
International Search Report, Application No. PCT/US02/26246, mailed May 21, 2003.
Statutory Declaration of Kari Alitalo, executed on Aug. 14, 2002, and accompanying Exhibits KA-1 and KA-2.
Statutory Declaration of Peter Adrian Walton Rogers, executed on Aug. 9, 2002.
Statutory Declaration of Francis John Ballard, executed on Jul. 16, 2002.
Statutory Declaration of Kari Alitalo, executed on Jul. 16, 2002, and accompanying Exhibit 1.
Statutory Declaration of Susan Power, executed on Mar. 22, 2002, and accompanying Appendices I to IV.
Statutory Declaration of Nicholas Kim Hayward, executed on Mar. 26, 2002.
Statutory Declaration of Stuart A. Aaronson, executed on Mar. 22, 2002, and accompanying Appendices I to III.
Statutory Declaration of Gary Baxter Cox, executed on Mar. 22, 2002, and accompanying Exhibit GBC24 (Statutory Declaration of Peter Adrian Walters, executed on Oct. 26, 2001).
Statutory Declaration of Frances John Ballard, executed on Dec. 12, 2001, and accompanying Exhibit 1.
Statutory Declaration of Kari Alitalo, executed on Sep. 24, 2001, and accompanying Exhibit 1 and 2.
Statutory Declaration of Peter Adrian Walton Rodgers, executed on Nov. 12, 2001, and accompanying Exhibits PAWR1 to PAWR14.
Statutory Declaration of John Stanley Mattick, executed on Dec. 12, 2000, and accompanying Exhibits JSM1 to JSM4.
Statutory Declaration of Nicholas Kim Hayward, executed on Dec. 8, 2000, and accompanying Exhibits NKH 1 and 2.
Statutory Declaration of Jennifer Ruth Gamble, executed on Dec. 12, 2000, and accompanying Exhibits JRG 1 to 3.
Statutory Declaration of Tom Rapoport, executed on Dec. 13, 2000, and accompanying Exhibits TP 1 and 2.
Statutory Declaration of Stuart A. Aaronson, executed on Dec. 14, 2000, and accompanying CV.
Statutory Declaration of Susan Power, executed on Dec. 13, 2000, and accompanying Appendices 1 to 2 and Figure 1.
Statutory Declaration of Gary Baxter Cox, executed on Dec. 13, 2000, and accompanying Exhibits GBC 1 to 23.
Statutory Declaration of Peter Adrian Walton Rogers, executed on Feb. 16, 2000 and accompanying Exhibit 1.
Statutory Declaration of Frances John Ballard, executed on Feb. 16, 2000, and accompanying Exhibit 1.
Statutory Declaration of Kari Alitalo, executed on Feb. 15, 2000, and accompanying Exhibits 1 to 3.
European Supplementary Search Report, Application No. EP 01963814, mailed Jul. 14, 2004.
Supplementary Partial European Search Report, Application No. EP 02726730, mailed Aug. 4, 2004.
Supplementary Partial European Search Report, Application No. EP 02721715, mailed Jan. 10, 2005.
Supplementary Partial European Search Report, Application No. EP 02721715, mailed Oct. 22, 2004.
EBI Accession No. AAW27553, Knappik et al., "Human Ab heavy chain variable region VH3 consensus," Jan. 23, 1998.
Supplementary European Search Report, Application No. EP 02726730, mailed Oct. 25, 2004.
Supplementary Partial European Search Report, Application No. EP 00905992, mailed Nov. 8, 2004.
English language abstract of JP 64-38100 A, cited as document FP2 on Form PTO/SB/08A, Derwent Accession No. 1989-088700/198912.
English language abstract of JP 2-117698 A, cited as document FP3 on Form PTO/SB/08A, Derwent Accession No. 1990-181364/199024.
Anderson, W.F., "Human gene therapy," *Nature* 392:25-30, Macmillan Magazines Ltd. (Apr. 1998).
Better et al., "*Escherichia coli* secretion of an active chimeric antibody fragment," *Science* 240:1041-1043, American Association for the Advancement of Science (1988).
Borg, J.-P., et al., "Biochemical characterization of two isoforms of FLT4, a VEGF receptor-related tyrosine kinase," *Oncogene* 10:973-984, Stockton Press (Mar. 1995).

Capogrossi, M.C., "Gene Therapy of Coronary Artery Disease," Project No. Z01 AG00811-01, Abstract (Jan. 1994).

Capogrossi, M.C., "Gene Therapy of Coronary Artery Disease," Project No. Z01 AG00811-02, Abstract (Jan. 1995).

Choi, I.H., et al., "Angiogenesis and Mineralization During Distraction Osteogenesis," *J. Korean Med. Sci. 17*:435-447, The Korean Academy of Medical Sciences (Aug. 2002).

Colwell et al., "Method for generating a high frequency of hybridomas producing monoclonal IgA antibodies," *Methods Enzymol. 121*:42-51, Academic Press (1986).

Danis, R.P., et al., "Anti-angiogenic therapy of proliferative diabetic retinopathy," *Exp. Opin. Pharma. 2*:395-407, Ashley Publications Ltd. (Mar. 2001).

Declaration of Dr. Kari Alitalo, In re of: U.S. Appl. No. 08/585,895, Alitalo et al., filed Jan. 12, 1996, submitted Nov. 26, 1997.

Dias, S., et al., "Vascular endothelial growth factor (VEGF)-C signaling through FLT-4 (VEGFR-3) mediates leukemic cell proliferation, survival, and resistance to chemotherapy," *Blood 99*:2179-2184, The American Society of Hematology (Mar. 2002).

Enholm, B., et al., "Vascular Endothelial Growth Factor-C: A Growth Factor for Lymphatic and Blood Vascular Endothelial Cells," *Trends Cardiovasc. Med. 8*:292-297, Elsevier Science Inc. (Oct. 1998).

Fan, T.-P.D., et al., "Controlling the vasculature: angiogenesis, anti-angiogenesis and vascular targeting of gene therapy," *Trends Pharmaco. Sci. 16*:57-66, Elsevier Science Ltd. (Feb. 1995).

Ferrara, N., "Vascular Endothelial Growth Factor and the Regulation of angiogenesis," *Recent Prog. Hormone Res. 55*:15-36, The Endocrine Society (Mar. 2000).

Halin, C. and Neri, D., "Antibody-Based Targeting of Angiogenesis," *Crit. Rev. Ther. Drug Carrier Syst. 18*:299-339, Begell House, Inc. (Aug. 2001).

Houck et al., "The vascular endothelial growth factor family: identification of a fourth molecular species and characterization of alternative splicing of RNA," *Mol. Endocrin. 5*:1806-1814, The Endocrine Society (1991).

Isner, J.M., et al., "Arterial Gene Therapy for Therapeutic Angiogenesis in Patients With Periperal Artery Disease," *Circulation 91*:2687-2692, American Heart Association, Inc. (Jun. 1995).

Isner, J.M. and Feldman, L.J., "Gene therapy for arterial disease," *Lancet 344*:1653-1654, The Lancet Ltd. (Dec. 1994).

Isner, J.M., et al., "Physiologic Assessment of Angiogenesis by Arterial Gene Therapy with Vascular Endothelial Growth Factor," *J. Cell. Biochem. (Suppl. 21A)*:378, Abstract C6-215, Wiley-Liss (Mar.-Apr. 1995).

Isner, J.M., "Therapeutic Angiogenesis in Vascular Medicine," Project No. R01 HL53354-01, Abstract (Mar. 1995).

Joosten et al., "The production of antibody fragments and antibody fusion proteins by yeasts and filamentous fungi," *Microbial Cell Fact. 2*:1, BioMed Central (Jan. 2003).

Kubo, H., et al., "Blockade of vascular endothelial growth factor receptor-3 signaling inhibits fibroblast growth factor-2-induced lymphangiogenesis in mouse cornea," *Proc. Natl. Acad. Sci. 99*:8868-8873, The National Academy of Sciences (Jun. 2002).

Kuzuya, M. and Kinsella, J.L., "Induction of Endothelial Cell Differentiation in Vitro by Fibroblast-Derived Soluble Factors," *Exp. Cell Res. 215*:310-318, Academic Press, Inc. (Dec. 1994).

Longo, R., et al., "Anti-angiogenic therapy: Rationale, challenges and clinical studies," *Angiogenesis 5*:237-256, Kluwer Academic Publishers (Dec. 2002).

Maher, P.A.., "Stimulation of Endothelial Cell Proliferation by Vanadate Is Specific for Microvascular Endothelial Cells," *J. Cell Physiol. 151*:549-554, Wiley-Liss, Inc. (1992).

Maynard, J. and Georgiou, G., "Antibody Engineering," *Annu. Rev. Biomed. Eng. 2*:339-376, Annual Reviews (Aug. 2000).

Mesri, E.A., et al., "Expression of Vascular Endothelial Growth Factor From a Defective Herpes Simplex Virus Type 1 Amplicon Vector Induces Angiogenesis in Mice," *Circulation Res. 76*:161-167, American Heart Association, Inc. (Feb. 1995).

Morea, V., et al., "Antibody Modeling: Implications for Engineering and Design," *Methods 20*:267-279, Academic Press (Mar. 2000).

Mühlhauser, J., et al., "In Vivo Gene Transfer into Porcine Cardiac Cells with a Replication-Deficient Recombinant Adenovirus Vector," *Circulation 88*:1-475, Abstract No. 2558, American Heart Association (Oct. 1993).

Mühlhauser, J., et al., "VEGF$_{165}$ Expressed by a Replication-Deficient Recombinant Adenovirus Vector Induces Angiogenesis In Vivo," *Circulation Res. 77*:1077-1086, American Heart Association, Inc (Dec. 1995).

Oikawa, T., et al., "Three Isoforms of Platelet-Derived Growth Factors All Have the Capability to Induce Angiogenesis In Vivo," *Biol. Pharm. Bull. 17*:1686-1688, Pharmaceutical Society of Japan (Dec. 1994).

Pajusola, K., et al., "Signalling properties of FLT4, a proteolytically processed receptor tyrosine kinase related to two VEGF receptors," *Oncogene 9*:3545-3555, Macmillan Press Ltd. (Dec. 1994).

Pepper, M.S., et al., "In Vitro Angiogenic and Proteolytic Properties of Bovine Lymphatic Endothelial Cells," *Exp. Cell Res. 210*:298-305, Academic Press, Inc. (Jan. 1994).

Plate, K.H., "From angiogenesis to lymphangiogenesis," *Nat. Med. 7*:151-152, Nature America, Inc. (Feb. 2001).

Schlaeppi et al., "Characterization of a new potent, in vivo neutralizing monoclonal antibody to human vascular endothelial growth factor," *J Cancer Res. Clin. Oncol. 125*:336-342 (1999).

Skerra et al., "Assembly of a functional immunoglobulin Fv fragment in *Escherichia coli.*" *Science 240*:1038-1041, American Association for the Advancement of Science (1988).

Spranger, J. and Pfeiffer, A.F.H., "New concepts in pathogenesis and treatment of diabetic retinopathy," *Exp. Clin. Endocrinol. Diabetes 109(Suppl. 2)*:S438-S450, J.A. Barth Verlag (2001).

Symes, J.F. and Sniderman, A.D., "Angiogenesis: potential therapy for ischaemic disease," *Curr. Opin. Lipidol. 5*:305-312, Current Science Ltd. (Aug. 1994).

Takeshita, S., et al., "In Vivo Evidence of Enhanced Angiogenesis Following Direct Arterial Gene Transfer of the Plasmid Encoding Vascular Endothelial Growth Factor," *Circulation 88*:I-476, Abstract No. 2565, American Heart Association (Oct. 1993).

Takeshita, S., et al., "Therapeutic Angiogenesis. A Single Intraarterial Bolus of Vascular Endothelial Growth Factor Augments Revascularization in a Rabbit Ischemic Hind Limb Model," *J. Clin. Invest. 93*:662-670, The American Society for Clinical Investigation, Inc. (Feb. 1994).

Van der Flier, M., et al., "Antibody neutralization of vascular endothelial growth factor (VEGF) fails to attenuate vascular permeability and brain edema in experimental pneumococcal meningitis," *J. Neuroimmunol. 160*:170-177, Elsevier B.V. (Mar. 2005).

Verma et al., "Gene therapy—promises, problems and prospects," *Nature 389*:239-242, Nature Publishing Company (Sep. 1997).

Walsh, D.A., "Angiogenesis and arthritis," *Rheumatology 38*:103-112, British Society for Rheumatology (Feb. 1999).

Walsh, D.A. and Pearson, C.I., "Angiogenesis in the pathogenesis of inflammatory joint and lung diseases," *Arthritis Res. 3*:147-153, BioMed Central Ltd. (Feb. 2001).

Williams, R.S., "Southwestern Internal Medicine Conference: Prospects for Gene Therapy of Ischemic Heart Disease," *Am. J. Med. Sci. 306*:129-136, Lippincott Williams & Wilkins (Aug. 1993).

Winkler, K., et al., "Changing the Antigen Binding Specificity by Single Point Mutations of an Anti-p24 (HIV-1) Antibody," *J. Immunol. 165*:4505-4514, The American Association of Immunologists (Oct. 2000).

Witzenbichler, B., et al., "Vascular Endothelial Growth Factor-C (VEGF-C/VEGF-2) Promotes Angiogenesis in the Setting of Tissue Ischemia," *Am. J. Pathol. 153*:381-394, American Society for Investigative Pathology, Inc. (Aug. 1998).

Yeung, P.K.F., "VEGF-2," *Curr. Opin. Invest. Drugs 2*:796-800, PharmaPress Ltd. (Jun. 2001).

NCBI Entrez, Accession No. AF010302, Mandriota S.J. and Pepper, M.S. (first available Jul. 16, 1997).

Letter from John J. Chicca II, Ph. D., Molecular Diagnostic Services, Inc. regarding a third progess report for a project entitled "Cloning and expression of VEGF-2 gene and the efficacy of VEGF-2 protein utilizing the 3-D collagen angiogenesis assay and proliferation," dated Feb. 16, 2006.

Letter from John J. Chicca II, Ph.D., Molecular Diagnostic Services, Inc. regarding a fourth progress report for a project entitled "Cloning and expression of VEGF-2 gene and the efficacy of VEGF-2 protein utilizing the 3-D collagen angiogenesis assay and proliferation," dated Mar. 14, 2006.

U.S. Appl. No. 11/730,696, inventors Rosen et al., filed Apr. 3, 2007 (not published).

Dermer, G.B., "Another Anniversary for the War on Cancer," *Bio/Technol. 12*:320, Wiley-VCH Verlag GmbH & Co. (Mar. 1994).

Duda, D.G., et al., "VEGF-targeted cancer therapy strategies: current progess, hurdles and future prospects," *Trends Molec. Med. 13(6)*:223-230, Elsevier Ltd. (Apr. 2007).

Gura, T., "Systems for Identifying New Drugs Are Often Faulty," *Science 278*(5340):1041-1042, American Association for the Advancement of Science (Nov. 1997).

Landolfi, N.F., et al., "The Integrity of the Ball-and-Socket Joint Between V and C Domains Is Essential for Complete Activity of a Humanized Antibody," *J. Immunol. 166*:1748-1754, The American Association of Immunologists (Feb. 2001).

Liu, Z., et al., "Fine mapping of the antigen-antibody interaction of scFv215, a recombinant antibody inhibiting RNA polymerase II from *Drosophila melanogaster*," *J. Mol. Recognit. 12*:103-111, John Wiley & Sons, Ltd. (Mar. 1999).

U.S. Appl. No. 12/078,569, inventors Rosen et al., filed Apr. 1, 2008 (not published).

U.S. Appl. No. 12/258,109, inventors Rosen et al., filed Oct. 24, 2008 (not published).

U.S. Appl. No. 12/258,140, inventors Alderson et al., filed Oct. 24, 2008 (not published).

Extended European Search Report for European Application No. 08153873.8, mailed Oct. 13, 2008, European Patent Office, Berlin, Germany.

Tobe, T., et al., "Evolution of Neovascularization in Mice with Overexpression of Vascular Endothelial Growth Factor in Photoreceptors," *Invest. Opthalmol. Vis. Sci. 39*:180-188, Association for Research in Vision and Ophthalmology (Jan. 1998).

Vinores, S.A., et al., "Cellular mechanisms of blood-retinal barrier dysfunction in macular edema," *Documenta Opthalmologica 97*:217-228, Kluwer Academic Publishers (Jan. 1999).

```
CGAGGCCACGGCTTATGCAAGCAAGATCTGGAGGAGCAGTTACGGTCTCTGTGTCCAGTGT

AGATGAACTCATGACTGTACTCTACCCAGAATATTGGAAAATGTACAAGTGTCAGCTAAG
              M  T  V  L  Y  P  E  Y  W  K  M  Y  K  C  Q  L  R

GAAAGGAGGCTGGCAACATAACAGAGAACAGGCCAACTCAAGGACAGAAGAGAC
 K  G  G  W  Q  H  N  R  E  Q  A  N  L  N  S  R  T  E  E  T

TATAAAATTGCTGCAGCACATTATAATACAGAGATCTTGAAAAGTATTGATAATGAGTG
 I  K  F  A  A  A  H  Y  N  T  E  I  L  K  S  I  D  N  E  W

GAGAAAGACTCAATGCCATGTGTGTATAGATGTGGGAAGGAGTTTGGAGT
 R  K  T  Q  C  M  P  R  E  V  C  I  D  V  G  K  E  F  G  V

CGCGACAAACACCTTCTTTAAACCTCCATGTGTCCGTCTACAGATGTGGGGGTTGCTG
 A  T  N  F  F  K  P  P  C  V  S  V  Y  R  C  G  G  C
```

FIG. 1A

```
CAATAGTGAGGGCTGCAGTGCATGAACACCAGCACGAGCTACCTCAGCAAGACGTTATT
 N  S  E  G  L  Q  C  M  N  T  S  T  S  Y  L  S  K  T  L  F

TGAAATTACAGTGCCTCTCTCTCAAGGCCCCAAACCAGTAACAATCAGTTTGCAATCA
 E  I  T  V  P  L  S  Q  G  P  K  P  V  T  I  S  F  A  N  H

CACTTCCTGCCGATGCATGTCTAAACTGGATGTTTACAGACAAGTTCATTCCATTATTAG
 T  S  C  R  C  M  S  K  L  D  V  Y  R  Q  V  H  S  I  I  R

ACGTTCCCTGCAGCAACACTACCAGTGTCAGGCAGCGAACAAGACCTGCCCCACCAA
 R  S  L  P  A  T  L  P  Q  C  Q  A  A  N  K  T  C  P  T  N

TTACATGTGGAATAATCACATCTGCAGATGCCTCAGGAAGATTTATGTTTTCCTC
 Y  M  W  N  N  H  I  C  R  C  L  A  Q  E  D  F  M  F  S  S

GGATGCTGGAGATGACTCAACAGATGGATTCCATGACATCTGTGGACCAAACAAGGAGCT
 D  A  G  D  D  S  T  D  G  F  H  D  I  C  G  P  N  K  E  L
```

FIG.1B

```
GGATGAAGAGACCTGTCAGTGTGTCTGCAGAGCGGGGCTTCGGCCTGCCAGCTGTGGACC
-----+---------+---------+---------+---------+---------+
 D  E  E  T  C  Q  C  V  C  R  A  G  L  R  P  A  S  C  G  P

CCACAAAGAACTAGACAGAAACTCATGCCAGTGTGTCTGTAAAACAAACTCTTCCCAG
-----+---------+---------+---------+---------+---------+
 H  K  E  L  D  R  N  S  C  Q  C  V  C  K  N  K  L  F  P  S

CCAATGTGGGGCCAACCGAGAATTTGATGAAAACACATGCCAGTGTGTATGTAAAGAAC
-----+---------+---------+---------+---------+---------+
 Q  C  G  A  N  R  E  F  D  E  N  T  C  Q  C  V  C  K  R  T

CTGCCCCAGAAATCAACCCCTAAATCCTGAAAATGTGCCTGTGAATGTACAGAAAGTCC
-----+---------+---------+---------+---------+---------+
 C  P  R  N  Q  P  L  N  P  G  K  C  A  C  E  C  T  E  S  P

ACAGAAATGCTTGTTAAAAGGAAAGAAGTTCCACCACCAAAACATGCAGCTGTTACAGACG
-----+---------+---------+---------+---------+---------+
 Q  K  C  L  L  K  G  K  K  F  H  H  Q  T  C  S  C  Y  R  R

GCCATGTACGAACCCGGCCAGAAGGCTTGTGAGCCAGGATTTCATATAGTGAAGAAGTGTG
-----+---------+---------+---------+---------+---------+
 P  C  T  N  R  Q  K  A  C  E  P  G  F  S  Y  S  E  E  V  C
```

FIG.1C

```
TCGTTGTGTCCCTTCATATTGGCAAAGACCACAAATGAGCTAAGATTGTACTGTTTCCA
----+---------+---------+---------+---------+---------+---------+
  R  C  V  P  S  Y  W  Q  R  P  Q  M  S

GTTCATCGATTTTCTATTATGGAAAACTGTGTTGCCACAGTAGAACTGTCTGTGAACAGA
----+---------+---------+---------+---------+---------+---------+

GAGACCCTTGTGGGTCCATGCTAACAAAGACACAAAGTCTGTCTTTCCTGAACCATGTGGA
----+---------+---------+---------+---------+---------+---------+

TAACTTTACAGAAATGGACTGGAGCTCATCTGCAAAAGGCCCTCTTGTAAAGACTGGTTTT
----+---------+---------+---------+---------+---------+---------+

CTGCCAATGACCAAACAGCCAAGATTTTCCTCTGTGATTTCTTTAAAAGAATGACTATA
----+---------+---------+---------+---------+---------+---------+

TAATTTATTTCCACTAAAAATATTGTTTCTGCATTCATTTTTATAGCAACAACAATTGGT
----+---------+---------+---------+---------+---------+---------+

AAAACTCACTGTGATCAATATTTTTATATCATGCAAAATATGTTTAAAATAAAATGAAAA
----+---------+---------+---------+---------+---------+---------+

TTGTATTATAAAAAAAAAAAAAAAA
----+---------+---------+
```

FIG.1D

```
                                                            50
Pdgfa   .MRTLACLLL LGCGYLAHVL AEEAEIPREV IERLARSQIH SIRDLQRLLE
Pdgfb   MNRCWA.LFL SLCCYLRLVS AEGDPIPEEL YEMLSDHSIR SFDDLQRLLH
Vegf    .....MNFLL SWVHWSLALL LY........ .......... .LHHAKWSQA
Vegf2   .......MTV LYPEYWKMYK CQ........ .......... .LRKGGWQHN 100
Pdgfa   IDSVGSEDSL DTSLRAHGVH ATKHVPEKRP LPIRRRSI.. .....EEAVP
Pdgfb   GDP.GEEDGA ELDLNMTRSH SGGELES... .LARGRRSLG SLTIAEPAMI
Vegf    APMAE..... ......GGGQ NHHEVVKFMD .VYQR..... .......... 
Vegf2   REQANLNSRT EETIKFAAAH YNTEILKSID NEWRK..... ..........

150
Pdgfa   AVCKTRTVIY EIPRSQVDPT SANFLIWPPC VEVKRCTGCC NTSSVKCQPS
Pdgfb   AECKTRTEVF EISRRLIDRT NANFLVWPPC VEVQRCSGCC NNRNVQCRPT
Vegf    SYCHPIETLV DIFQEYPDEI ..EYIFKPSC VPLMRCGGCC NDEGLECVPT
Vegf2   TQCMPREVCI DVGKEFGVAT ..NTFFKPPC VSVYRCGGCC NSEGLQCMNT 200
Pdgfa   RVHHRSVKVA KVEYVRKKPK LKEVQVRLEE HLECAC.... AT........
Pdgfb   QVQLRPVQVR KIEIVRKKPI FKKATVTLED HLACKC.... ETVAAARPVT
Vegf    EESNITMQIM RIK.PH..QG QHIGEMSFLQ HNKCECRPKK DRARQEKKSV
Vegf2   STSYLSKTLF EIT.VPLSQG PKPVTISFAN HTSCRCMSKL DVYRQVHSII
```

FIG. 2A

```
         201                                                      250
Pdgfa    ....TSLNPD YREEDTDVR. .......... .......... ..........
Pdgfb    RSPGGSQEQR AKTPQTRVTI RTVRVRRPPK GKHRKFKHTH DKTALKETLG
Vegf     RGK....... .GKGQKRKRK KSRYKSWSVY VGARCCLMPW SLPGPHP...
Vegf2    RRSLPATLPQ CQAANKTCPT NYMWNNHICR CLAQEDFMFS SDAGDDSTDG 251                                                      300
Pdgfa    .......... .......... .......... .......... ..........
Pdgfb    A......... .......... .......... .......... ..........
Vegf     ....CGP... .......... ......CSE RRKHLFVQDP QTCKCSCKNT
Vegf2    FHDICGPNKE LDEETCQCVC RAGLRPASCG PHKEL...DR NSCQCVCKNK 301                                                      350
Pdgfa    .......... .......... .......... .......... ..........
Pdgfb    .......... .......... .......... .......... ..........
Vegf     ..DSRCKARQ LELNERTCRC DKPRR..... .......... ..........
Vegf2    .EFDENTCQC .VCKRTCPRNQ PLNPGKCACE CTESPQRCLL 351                                       398
Pdgfa    .......... .......... .......... ........
Pdgfb    .......... .......... .......... ........
Vegf     .......... .......... .......... ........
Vegf2    LFPSQCGANR SCYRRPCTNR QKACEPGFSY SEEVCRCVPS YWQRPQMS
```

FIG. 2B

| PERCENTAGE (%) OF AMINO ACID IDENTITIES BETWEEN EACH PAIR OF GENES IS SHOWN IN THE FOLLWING TABLE | | | | |
|---|---|---|---|---|
| | PDGFα | PDGFβ | VEGF | VEGF2 |
| PDGFβ | 48.0 | | | |
| VEGF | 20.7 | 22.7 | | |
| VEGF2 | 23.5 | 22.4 | 30.0 | |

FIG.3

Expression of VEGF2 mRNA in Human Breast Tumor Cells

1. normal breast tissue
2. breast tumor tissue
3-9. breast tumor cell lines.

| Lane 1: | 14-C and rainbow M.W. marker |
| Lane 2: | FGF control |
| Lane 3: | VEGF2 (M13-reverse $ forward primers) |
| Lane 4: | VEGF2 (M13-reverse & VEGF-F4 primers) |
| Lane 5: | VEGF2 (M13-reverse & VEGF-F5 primers) |

ANTIBODIES TO VASCULAR ENDOTHELIAL GROWTH FACTOR 2 AND METHODS OF USING SAME

This application is a continuation of U.S. application Ser. No. 10/060,523, filed Feb. 1, 2002, now abandoned; which is a continuation U.S. application Ser. No. 09/618,451, filed Jul. 18, 2000, now abandoned; which is a continuation of U.S. application Ser. No. 09/257,918, filed Feb. 26, 1999, now abandoned; which is a division of U.S. application Ser. No. 08/824,996, filed Mar. 27, 1997, now U.S. Pat. No. 5,935,820, issued Aug. 10, 1999; which is a division of U.S. application Ser. No. 08/207,550, filed Mar. 8, 1994, now abandoned; all of which are hereby incorporated by reference in their entirety.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human vascular endothelial growth factor 2 (VEGF2). The invention also relates to inhibiting the action of such polypeptide.

The formation of new blood vessels, or angiogenesis, is essential for embryonic development, subsequent growth, and tissue repair. Angiogenesis is an essential part of the growth of human solid cancer, and abnormal angiogenesis is associated with other diseases such as rheumatoid arthritis, psoriasis, and diabetic retinopathy (Folkman, J. and Klagsbrun, M., Science 235:442-447, (1987)).

Several factors are involved in angiogenesis. Both acidic and basic fibroblast growth factor molecules that are mitogens for endothelial cells and other cell types. Angiotropin and angiogenin can induce angiogenesis, although their functions are unclear (Folkman, J., 1993, Cancer Medicine pp. 153-170, Lea and Febiger Press). A highly selective mitogen for vascular endothelial cells is vascular endothelial growth factor or VEGF (Ferrara, N., et al., Endocr. Rev. 13:19-32, (1992)). Vascular endothelial growth factor is a secreted angiogenic mitogen whose target cell specificity appears to be restricted to vascular endothelial cells. The murine VEGF gene has been characterized and its expression pattern in embryogenesis has been analyzed. A persistent expression of VEGF was observed in epithelial cells adjacent to fenestrated endothelium, e.g., in choroid plexus and in kidney glomeruli. The data was consistent with a role of VEGF as a multifunctional regulator of endothelial cell growth and differentiation. Breier, G. et al. Development, 114:521-532 (1992).

VEGF can promote angiogenesis. VEGF shares sequence homology with human platelet-derived growth factor, PDGFα and PDGFβ (Leung, D. W., et al., Science, 1306-1309, (1989)). The extent of homology is about 21% and 24% respectively. Eight cysteine residues are conserved between all three members. Although they are similar, there are specific differences between VEGF and PDGF. While PDGF is a major growth factor for connective tissue, VEGF is highly specific for endothelial cells. VEGF is also known as vascular permeability factor (VPM) and follicle stellate-derived growth factor. It is a heparin-binding dimeric polypeptide.

VEGF has four different forms of 121, 165, 189 and 206 amino acids due to alternative splicing. VEGF121 and VEGF165 are soluble and are capable of promoting angiogenesis, whereas VEGF189 and VEGF206 are bound to heparin containing proteoglycans in the cell surface. The temporal and spatial expression of VEGF has been correlated with physiological proliferation of the blood vessels (Gajdusek, C. M., and Carbon, S. J., Cell Physiol., 139:570-579, (1989)); McNeil, P. L., Muthukrishnan, L., Warder, E., D'Amore, P. A., J. Cell. Biol., 109:811-822, (1989)). Its high affinity binding sites are localized only on endothelial cells in tissue sections (Jakeman, L. B., et al., Clin. Invest. 89:244-253, (1989)). The factor can be isolated from pituitary cells and several tumor cell lines, and has been implicated in some human gliomas (Plate, K. H. Nature 359:845-848, (1992)).

Interestingly, expression of VEGF121 or VEGF165 confers on Chinese hamster ovary cells the ability to form tumors in nude mice (Ferrara, N., et al., J. Clin. Invest. 91:160-170, (1993)). Finally, the inhibition of VEGF function by anti-VEGF monoclonal antibodies was shown to inhibit tumor growth in immune-deficient mice (Kim, K. J., Nature 362:841-844, (1993)).

Vascular permeability factor, also known as VEGF, has also been found to be responsible for persistent microvascular hyperpermeability to plasma proteins even after the cessation of injury, which is a characteristic feature of normal wound healing. This suggests that VPF (or VEGF) is an important factor in wound healing. Brown, L. F. et al., J. Exp. Med., 176:1375-9 (1992).

U.S. Pat. No. 5,073,492, issued Dec. 17, 1991 to Chen et al., discloses a method for synergistically enhancing endothelial cell growth in an appropriate environment which comprises adding to the environment, VEGF, effectors and serum-derived factor. Also, vascular endothelial cell growth factor C sub-unit DNA has been prepared by polymerase chain reaction techniques. The DNA encodes a protein that may exist as either a heterodimer or homodimer. The protein is a mammalian vascular endothelial cell mitogen and, as such, is useful for the promotion of vascular development and repair, as disclosed in European Patent Application No. 92302750.2, published Sep. 30, 1992.

In accordance with one aspect of the present invention, there is provided a novel mature polypeptide which is a VEGF2 as well as fragments, analogs and derivatives thereof. The VEGF2 of the present invention is of human origin.

In accordance with another aspect of the present invention, there are provided polynucleotides (DNA or RNA) which encode such polypeptides.

In accordance with still another aspect of the present invention, there is provided a process for producing such polypeptide by recombinant techniques.

In accordance with yet a further aspect of the present invention, there is provided a process for utilizing such polypeptide, or polynucleotide encoding such polypeptide, for therapeutic purposes, for example, as a wound-healing agent, to promote growth of damaged bone and tissue and promote endothelialization as well as for diagnosis of tumors, cancer therapy and to identify and isolate unknown receptors of VEGF2.

In accordance with yet another aspect of the present invention, there is provided an antibody against the VEGF2 and a process for producing such antibody.

In accordance with yet another aspect of the present invention, there are provided antagonist/inhibitors to VEGF2, which may be used to inhibit the action of such polypeptide, for example, to prevent tumor angiogenesis.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A-D (FIG. 1A shows the first portions of the polynucleotide sequence encoding VEGF2 and the amino acid sequence for VEGF2, and FIGS. 1B, 1C and 1D, respectively continue with the sequential portions of each sequence began in FIG. 1A) collectively depict the polynucleotide sequence (SEQ ID NO:1) which encodes VEGF2, and the corresponding amino acid sequence (SEQ ID NO:2) for the VEGF2 polypeptide comprising 350 amino acid residues of which approximately the first 24 amino acids represent the leader sequence. The standard one-letter codes are utilized to depict the amino acid residues encoded by the polynucleotide triplets.

FIGS. 2A-B collectively depict polypeptide sequences in alignment and show the alignment of VEGF2 with the other growth factor PDGFα, PDGFβ, and VEGF. FIG. 2A depicts N-terminal portions of the polypeptide sequences and FIG. 2A continues with C-terminal portions of the polypeptide sequences. The four lines in each comparative row depict, respectively, the PDGFα polypeptide sequence (SEQ ID NO:7), the PDGFβ polypeptide sequence (SEQ ID NO:8), the VEGF polypeptide sequence (SEQ ID NO:9) and the VEGF2 polypeptide sequence. The amino acid residues are illustrated in FIGS. 2A and 2B by the standard one-letter codes.

FIG. 3 shows, in table-form, the percent homology between PDGFα, PDGFβ, VEGF and VEGF2.

Figure 4:
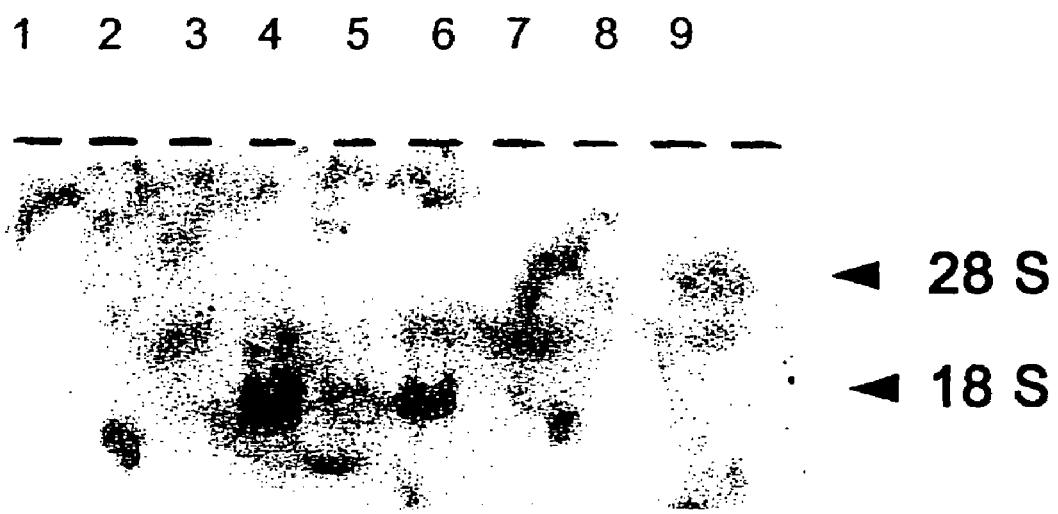
FIG. 4 shows the presence of mRNA for VEGF2 in breast tumor cell lines.

In accordance with one aspect of the present invention, there is provided an isolated nucleic acid (polynucleotide) which encodes for the mature polypeptide having the deduced amino acid sequence of SEQ ID NO:2 or for the mature polypeptide encoded by the cDNA of the clone deposited as ATCC Deposit No. 75698, on Mar. 4, 1994, with ATCC, 10801 University Boulevard, Manassas, Va. 20110-2209. Since the strain referred to is being maintained under the terms of the Budapest Treaty, it will be made available to a patent office signatory to the Budapest Treaty. If a patent should issue which is directed to the present invention, upon the issuance of such a patent the deposited strain of ATCC 75698 will be irrevocably and without restriction released to the public, excepting for those restrictions permitted by enforcement of the patent.

A polynucleotide encoding a polypeptide of the present invention may be obtained from early stage human embryo (week 8 to 9) osteoclastomas, adult heart or several breast cancer cell lines. The polynucleotide of this invention was discovered in a cDNA library derived from early stage human embryo week 9. It is structurally related to the VEGF/PDGF family. It contains an open reading frame encoding a protein of about 350 amino acid residues of which approximately the first 24 amino acid residues are likely to be leader sequence such that the mature protein comprises 326 amino acids, and which protein exhibits the highest homology to vascular endothelial growth factor (30% identity), followed by PDGFα (23%) and PDGFβ (22%), (see FIG. 3). It is particularly important that all eight cysteines are conserved within all four members of the family (see boxed areas of FIG. 2). In addition, the signature for the PDGF/VEGF family, PXCVXXXRCXGCCN, (SEQ ID NO:3) is conserved in VEGF2 (see FIG. 2). The homology between VEGF2, VEGF and the two PDGFs is at the protein sequence level. No nucleotide sequence homology can be detected, and therefore, it would be difficult to isolate the VEGF2 through simple approaches such as low stringency hybridization.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in SEQ ID NO:1 or that of the deposited clone or may be a different coding sequence which coding sequence, as a result of the redundancy or degeneracy of the genetic code, encodes the same, mature polypeptide as the DNA of SEQ ID NO:1 or the deposited cDNA.

The polynucleotide which encodes for the mature polypeptide of FIG. 1 or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 or the same mature polypeptide encoded by the cDNA of the deposited clone as well as variants of such polynucleotides which variants encode for a fragment, derivative or analog of the polypeptide of FIG. 1 or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in SEQ ID NO:1 or of the coding sequence of the deposited clone. As known in the art, an allelic variant is an alternate form of a polynucleotide sequence which have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of SEQ ID NO:2 or the deposited cDNA.

The deposit(s) referred to herein will be maintained under the Budapest Treaty on the International Recognition of the Deposit of Microorganisms for the purposes of Patent Procedure. These deposits are provided merely as a convenience and are not an admission that a deposit is required under 35 U.S.C. § 112. The sequence of the polynucleotides contained in the deposited materials, as well as the amino acid sequence of the polypeptides encoded thereby, are incorporated herein by reference and are controlling in the event of any conflict with the description of sequences herein. A license may be required to make, use or sell the deposited materials, and no such license is hereby granted.

The present invention further relates to a VEGF2 polypeptide which has the deduced amino acid sequence of SEQ ID NO:2 or which has the amino acid sequence encoded by the deposited cDNA, as well as fragments, analogs and derivatives of such polypeptide.

The terms "fragment," "derivative" and "analog" when referring to the polypeptide of SEQ ID NO:2 or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of SEQ ID NO:2 or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the VEGF2 genes. The culture conditions, such as temperature, pH and the like, are those previously used with the host cell selected for expression, and will be apparent to the ordinarily skilled artisan.

The polynucleotide of the present invention may be employed for producing a polypeptide by recombinant techniques. Thus, for example, the polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used as long as it is replicable and viable in the host.

As hereinabove described, the appropriate DNA sequence may be inserted into the vector by a variety of procedures. In general, the DNA sequence is inserted into an appropriate restriction endonuclease sites by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as herein above described, as well as an appropriate promoter or control sequence, may be employed to transform an appropriate host to permit the host to express the protein. As representative examples of appropriate hosts, there may be mentioned: bacterial cells, such as *E. coli Salmonella typhimurium Streptomyces*; fungal cells, such as yeast; insect cells, such as *Drosophila* and *Sf9*; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE-9 (Qiagen), pBs, phagescript, PsiX174, pBluescript SK, pBsKS, pNH8a, pNH16a, pNH18a, pNH46a (Stratagene); pTrc99A, pKK223-3, pKK233-3, pDR540, PRIT5 (Pharmacia). Eukaryotic: pWLneo, pSV2cat, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, 1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook. et al., Molecular Cloning: A Laboratory Manual, Second Edition, (Cold Spring Harbor, N.Y., 1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts, described by Gluzman, Cell, 23:175

(1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

VEGF2 is recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. It is preferred to have low concentrations (approximately 0.1-5 mM) of calcium ion present during purification (Price, et al., J. Biol. Chem., 244:917 (1969)). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated.

VEGF2 is useful as a wound healing agent, particularly where it is necessary to re-vascularize damaged tissues, or where new capillary angiogenesis is important. Therefore, it may be used for treatment of full-thickness wounds such as dermal ulcers, including pressure sores, venous ulcers, and diabetic ulcers. In addition, it can be used in the treatment of full-thickness burns and injuries where angiogenesis is desired to prepare the burn in injured sites for a skin graft and flap. In this case, it should be applied directly at the sites. Similar, VEGF2 can be used in plastic surgery when reconstruction is required following a burn, other trauma, or even for cosmetic purposes.

VEGF2 may also be used to induce the growth of damaged bone, periodontium or ligament tissue. It may be used in periodontal disease where VEGF2 is applied in a methylcellulose gel to the roots of the diseased teeth, the treatment could lead to the formation of new bone and cementum with collagen fiber ingrowths. It can be used for regenerating supporting tissues of teeth, including alveolar bone, cementum and periodontal ligament, that have been damaged by disease and trauma.

Since angiogenesis is important in keeping wounds clean and non-infected, VEGF2 may be used in association with surgery and following the repair of cuts. It should be particularly useful in the treatment of abdominal wounds where there is a high risk of infection.

VEGF2 can be used for the promotion of endothelialization in vascular graft surgery. In the case of vascular grafts using either transplanted or synthetic material, VEGF2 can be applied to the surface of the graft or at the junction to promote the growth of the vascular endothelial cells. One derivation of this is that VEGF2 can be used to repair the damage of myocardial infarction and other occasions where coronary bypass surgery is needed by stimulating the growth of the transplanted tissue. Related to this is the use of VEGF2 to repair the cardiac vascular system after ischemia.

The identification of VEGF2 can be used for the generation of certain inhibitors of vascular endothelial growth factor. Since angiogenesis and neovascularization are essential steps in solid tumor growth, inhibition of angiogenic activity of the vascular endothelial growth factor is very useful to prevent the further growth, retard, or even regress solid tumors. Although the level of expression of VEGF2 is extremely low in normal tissues including breast, it can be found expressed at moderate levels in at least two breast tumor cell lines that are derived from malignant tumors. It is, therefore, possible that VEGF2 is involved in tumor angiogenesis and growth.

VEGF2 can be used for in vitro culturing of vascular endothelial cells, where it can be added to the conditional medium to a concentration from 10 pg/ml to 10 ng/ml.

The polypeptide of the present invention may also be employed in accordance with the present invention by expression of such polypeptide in vivo, which is often referred to as "gene therapy."

Thus, for example, cells such as bone marrow cells may be engineered with a polynucleotide (DNA or RNA) encoding for the polypeptide ex vivo, the engineered cells are then provided to a patient to be treated with the polypeptide. Such methods are well-known in the art. For example, cells may be engineered by procedures known in the art by use of a retroviral particle containing RNA encoding for the polypeptide of the present invention.

Similarly, cells may be engineered in vivo for expression of the polypeptide in vivo, for example, by procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such methods should be apparent to those skilled in the art from the teachings of the present invention. For example, the expression vehicle for engineering cells may be other than a retroviral particle, for example, an adenovirus, which may be used to engineering cells in vivo after combination with a suitable delivery vehicle.

The polypeptide of the present invention may be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptide of the present invention may be employed on conjunction with other therapeutic compounds.

The pharmaceutical compositions may be administered in a convenient manner, such as the oral, and intravenous routes, and is preferably administered topically. The amounts and dosage regimens of VEGF2 administered to a subject will depend on a number of factors, such as the mode of administration, the nature of the condition being treated, the body weight of the subject being treated and the judgment of the prescribing physician. Generally speaking, it is given, for example, in therapeutically effective doses of at least about 10 μg/kg body weight and, in most cases, it would be administered in an amount not in excess of about 8 mg/kg body weight per day and preferably the dosage is from about 10 μg/kg body weight to about 1 mg/kg body weight daily, taking into the account the routes of administration, symptoms, etc.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphism's) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15-25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clone from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques. Pergamon Press, New York (1988).

Once a sequence has been mapped to a precise chromosomal location, the physical position of the sequence on the chromosome can be correlated with genetic map data. (Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The present invention is further directed to inhibiting VEGF2 in vivo by the use of antisense technology. Antisense technology can be used to control gene expression through triple-helix formation or antisense DNA or RNA, both of which methods are based on binding of a polynucleotide to DNA or RNA. For example, the 5' coding portion of the mature polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription (triple helix—see Lee et al, Nucl. Acids Res., 6:3073 (1979); Cooney et al, Science, 241:456 (1988); and Dervan et al, Science, 251: 1360 (1991), thereby preventing transcription and the production of VEGF2. The antisense RNA oligonucleotide hybridizes to the mRNA in vivo and blocks translation of an mRNA molecule into the VEGF2 (antisense—Okano, J. Neurochem., 56:560 (1991); Oligodeoxynucleotides as Antisense Inhibitors of Gene Expression, CRC Press, Boca Raton, Fla. (1988)).

Alternatively, the oligonucleotides described above can be delivered to cells by procedures in the art such that the antisense RNA or DNA may be expressed in vivo to inhibit production of VEGF2 in the manner described above.

Antisense constructs to VEGF2, therefore, may inhibit the angiogenic activity of the VEGF2 and prevent the further growth or even regress solid tumors, since angiogenesis and neovascularization are essential steps in solid tumor growth. These antisense constructs may also be used to treat rheumatoid arthritis, psoriasis and diabetic retinopathy which are all characterized by abnormal angiogenesis.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptide corresponding to a sequence of the present invention can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495-497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to immunogenic polypeptide products of this invention.

Neutralization antibodies can be identified and applied to mask the vascular endothelial growth factor, and that has been shown in mice model systems against VEGF. VEGF2 can also be inactivated by certain dominant negative mutants within the gene itself. It is known that both PDGFα and β form either heterodimers or homodimers, and VEGF forms homodimers. Similar interaction between VEGF2 could be expected. These antibodies therefore may be used to block the angiogenic activity of VEGF2 and retard the growth of solid tumors. These antibodies may also be used to treat inflammation caused by the increased vascular permeability which results from the presence of VEGF2.

These antibodies may further be used in an immunoassay to detect the presence of tumors in certain individuals. Enzyme immunoassay can be performed from the blood sample of an individual. Elevated levels of of VEGF2 can be considered diagnostic of cancer.

The present invention is also directed to antagonist/inhibitors of the polypeptides of the present invention. The antagonist/inhibitors are those which inhibit or eliminate the function of the polypeptide.

Thus, for example, antagonists bind to a polypeptide of the present invention and inhibit or eliminate its function. The antagonist, for example, could be an antibody against the polypeptide which binds to the polypeptide or, in some cases, an oligonucleotide. An example of an inhibitor is a small molecule which binds to and occupies the catalytic site of the polypeptide thereby making the catalytic site inaccessible to substrate such that normal biological activity is prevented. Examples of small molecules include but are not limited to small peptides or peptide-like molecules.

Figure 5:
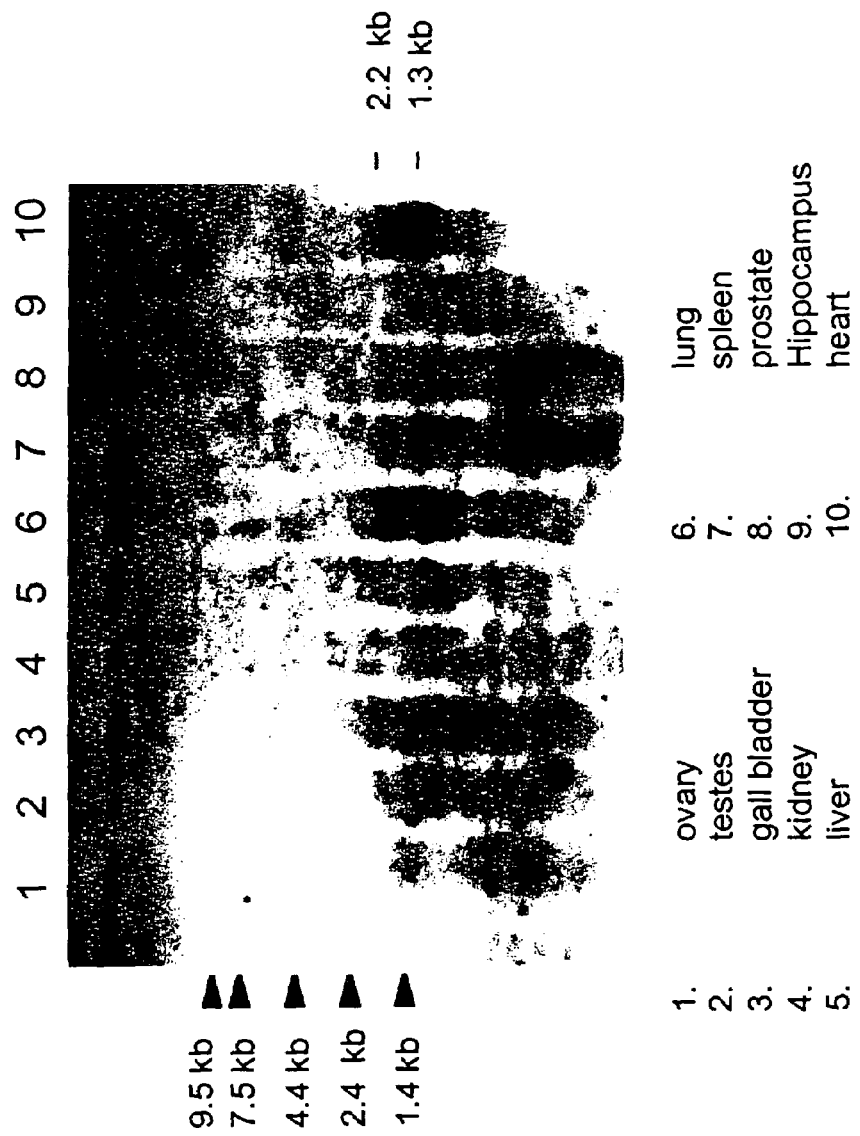
FIG. 5 depicts the results of a Northern blot analysis of VEGF2 in human adult tissues.

Truncated versions of VEGF2 can also be produced that are capable of interacting with wild type VEGF2 form dimers that fail activate endothelial cell growth, therefore inactivated the endogenous VEGF2. Or, mutant forms of VEGF2 form dimers themselves and occupies the ligand binding domain of the proper tyrosine Kinase receptors on the target cell surface, but fail to activate the cell growth.

Alternatively, antagonists to the polypeptides of the present invention may be employed which bind to the receptors to which a polypeptide of the present invention normally binds. The antagonists may be closely related proteins such that they recognize and bind to the receptor sites of the natural protein, however, they are inactive forms of the natural protein and thereby prevent the action of VEGF2 since receptor sites are occupied. In these ways, the action of the VEGF2 is prevented and the antagonist/inhibitors may be used therapeutically as an anti-tumor drug by occupying the receptor sites of tumors which are recognized by VEGF2 or by inactivating VEGF2 itself. The antagonist/inhibitors may also be used to prevent inflammation due to the increased vascular permeability action of VEGF2. The antagonist/inhibitors may also be used to treat solid tumor growth, diabetic retinopathy, psoriasis and rheumatoid arthritis.

The antagonist/inhibitors may be employed in a composition with a pharmaceutically acceptable carrier, e.g., as hereinabove described.

The present invention will be further described with reference to the following examples; however, it is to be understood that the present invention is not limited to such examples. All parts or amounts, unless otherwise specified, are by weight.

In order to facilitate understanding of the following examples, certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a poly-acrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described by the method of Graham, F. and Van der Eb, A., Virology, 52:456-457 (1973).

EXAMPLE 1

Expression Pattern of VEFG2 in Human Tissues and Breast Cancer Cell Lines

Northern blot analysis was carried out to examine the levels of expression of VEGF2 in human tissues and breast cancer cell lines in human tissues. Total cellular RNA samples were isolated with RNAzol™ B system (Biotecx Laboratories, Inc.). About 10 μg of total RNA isolated from each breast tissue and cell line specified was separated on 1% agarose gel and blotted onto a nylon filter, (Molecular Cloning, Sambrook Fritsch, and Maniatis, Cold Spring Harbor Press, 1989). The labeling reaction was done according to the Stratagene Prime-It kit with 50 ng DNA fragment. The labeled DNA was purified with a Select-G-50 column from 5' Prime—3 Prime, Inc. The filter was then hybridized with radioactive labeled full length VEGF2 gene at 1,000,000 cpm/ml in 0.5 M NaPO$_4$ and 7% SDS overnight at 65° C. After wash twice at room temperature and twice at 60° C. with 0.5×SSC, 0.1% SDS, the filters were then exposed at −70° C. overnight with intensifying screen. A message of 1.6 Kb was observed in 2 breast cancer cell lines. Lane #4 represents a very tumorigenic cell line that is estrogen independent for growth. See FIG. 4. Also, 10 μg of total RNA from 10 human adult tissues were separated on an agarose gel and blotted onto a nylon filter. The filter was then hybridized with radioactively labeled VEGF2 probe in 7% SDS, 0.5 M NaPO$_4$, pH 7.2; 1% BSA overnight at 65° C. Following was in 0.2×SSC at 65° C., the filter was exposed to film for 24 days at −70° C. with intensifying screen. See FIG. 5.

EXAMPLE 2

Expression of VEGF2 by in Vitro Transcription and Translation

The VEGF2 cDNA was transcribed and translated in vitro to determine the size of the translatable polypeptide encoded by the full length and partial VEGF2 cDNA. The full length and partial cDNA inserts of VEGF2 in the pBluescript SK vector were amplified by PCR with three pairs of primers, 1) M13-reverse and forward primers; 2) M13-reverse primer and VEGF primer F4; 3) M13-reverse primer and VEGF primer F5. The sequence of these primers are as follows.

M13-3 reverse primer:
5'-ATGCTTCCGGCTCGTATG-3' (SEQ ID NO:4)
This sequence is located upstream of the 5' end of the VEGF2 cDNA insert in the pBluescript vector and is in an anti-sense orientation as the cDNA. A T3 promoter sequence is located between this primer and the VEGF2 cDNA.

M13-2 forward primer:
5'-GGGTTTTCCCAGTCACGAC-3' (SEQ ID NO:5)
This sequence is located downstream of the 3' end of the VEGF2 cDNA insert in the pBluescript vector and is in an anti-sense orientation as the cDNA insert.

VEGF primer F4:
5'-CCACATGGTTCAGGAAAGACA-3' (SEQ ID NO:6)
This sequence is located within the VEGF2 cDNA in an anti-sense orientation from bp 1259-1239, which is about 169 bp away from the 3' end of the stop codon and about 266 bp before the last nucleotide of the cDNA.

PCR reaction with all three pairs of primers produce amplified products with T3 promoter sequence in front of the cDNA insert. The first and third pairs of primers produce PCR products that encode the full polypeptide of VEGF2. The second pair of primers produce PCR product that misses 36 amino acids coding sequence at the C-terminus of the VEGF2 polypeptide.

Approximately 0.5 ug of PCR product from first pair of primers, 1 ug from second pair of primers, 1 ug from third pair of primers were used for in vitro transcription/translation. The in vitro transcription/translation reaction was performed in a 25 ul of volume, using the T$_N$T™ Coupled Reticulocyte Lysate Systems (promega, CAT# L4950). Specifically, the reaction contains 12.5 ul of T$_N$T rabbit reticulocyte lysate 2 ul of T$_N$T reaction buffer, 1 ul of T3 polymerase, 1 ul of 1 mM amino acid mixture (minus methionine), 4 ul of $^{35}$S -methionine (>1000 Ci/mmol, 10 mCi/ml), 1 ul of 40 U/ul; RNasin ribonuclease inhibitor, 0.5 or 1 ug of PCR products. Nuclease-free H$_2$0 were added to bring the me to 25 ul. The reaction was incubated at 30° C. for 2 hours. Five microliters of the reaction product was analyzed on a 4-20% gradient SDS-PAGE gel. After fixing in 25% isopropanol and 10% acetic acid, the gel was dried and exposed to an X-ray film overnight at 70° C.

Figure 6:
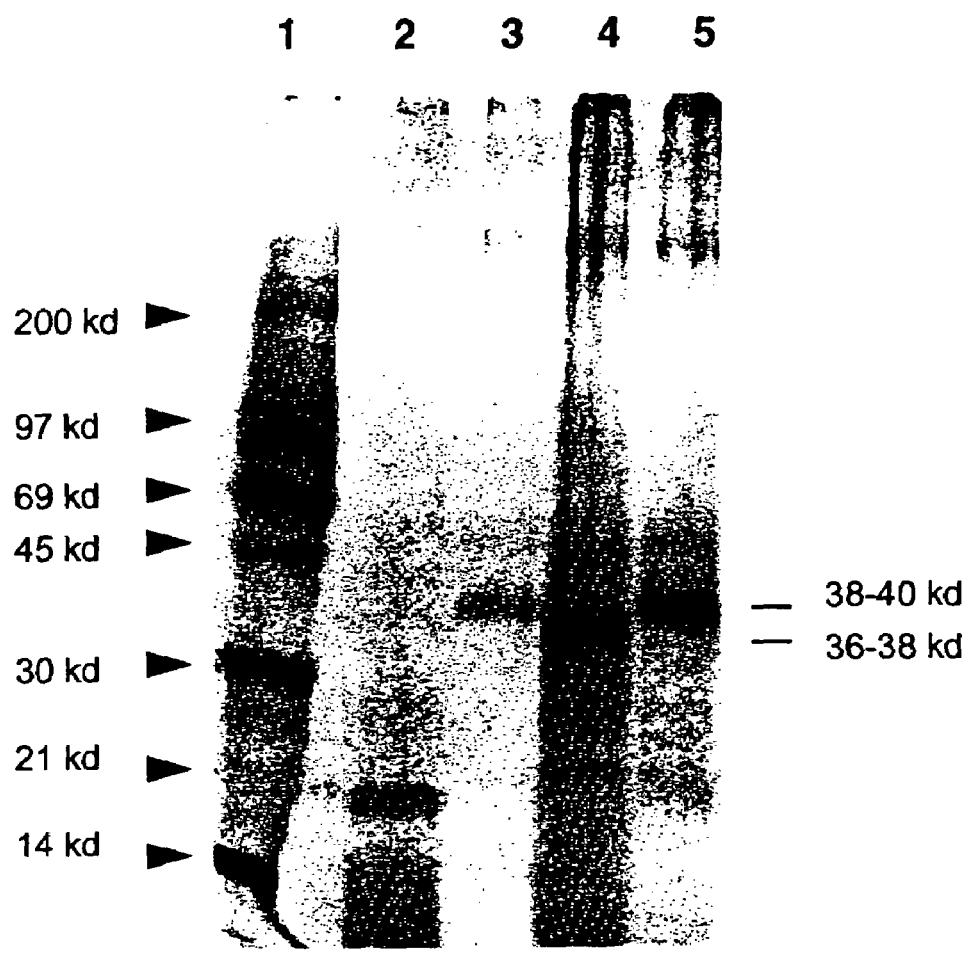
FIG. 6 shows the results of running VEGF2 and SDS-PAGE gel after in vitro transcription/translation. The full length and partial VEGF2 cDNA were transcribed and translated in a coupled reaction in the presence of $^{35}$S-methionine. The translated products were analyzed by 4-20% gradient SDS PAGE and exposed to X-ray film.

As shown in FIG. 6, PCR products containing the full length VEGF2 cDNA and the cDNA missing 266 bp in the 3' un-translated region (3'-UTR) produced the same length of translated products, whose molecular weights are estimated to be 38-40 kD (lanes 1 & 3). The cDNA missing all the 3'UTR and missing sequence encoding the C-terminal 36 amino acids was translated into a polypeptide with an estimated molecular weight of 36-38 kD (lane 2).

What is claimed is:

1. An antagonist against a polypeptide selected from the group consisting of:
   (i) a VEGF2 polypeptide having the amino acid sequence of SEQ ID NO: 2; and
   (ii) a VEGF2 polypeptide encoded by the cDNA of ATCC Deposit No. 75698;
   wherein said antagonist is an antibody.

2. A composition comprising the antagonist of claim 1 and a suitable pharmaceutical carrier or excipient.

3. A method for the treatment of a patient having a need to inhibit VEGF2 activity comprising administration of an effective amount of the antagonist of claim 1.

4. A method of inhibiting angiogenesis in a patient comprising administration of an effective amount of the antagonist of claim 1.

5. A method of treating inflammation in a patient comprising administration of an effective amount of the antagonist of claim 1.

6. A method for the treatment of rheumatoid arthritis, psoriasis or diabetic neuropathy in a patient comprising administration of an effective amount of the antagonist of claim 1.

7. A method for the treatment of solid tumors in a patient comprising administration of an effective amount of the antagonist of claim 1.

8. The method of claim 7, wherein tumor angiogenesis is inhibited.

9. A method for inhibition of endothelialization in a patient comprising administration of an effective amount of the antagonist of claim 1.

10. An antagonist against a polypeptide selected from the group consisting of:
   (a) a polypeptide comprising amino acids 61 to 74 of SEQ ID NO:2;
   (b) a polypeptide comprising amino acids 38 to 118 of SEQ ID NO:2;
   (c) a polypeptide comprising amino acids 1 to 326 of SEQ ID NO:2; and
   (d) a polypeptide comprising amino acids −24 to 326 of SEQ ID NO:2, wherein the antagonist is an antibody that inhibits the activity of VEGF2.

11. A composition comprising the antagonist of claim 10 and a suitable pharmaceutical carrier or excipient.

12. A method for the treatment of a patient having a need to inhibit VEGF2 activity comprising administration of an effective amount of the antagonist of claim 10.

13. A method of inhibiting angiogenesis in a patient comprising administration of an effective amount of the antagonist of claim 10.

14. A method of treating inflammation in a patient comprising administration of an effective amount of the antagonist of claim 10.

15. A method for the treatment of rheumatoid arthritis, psoriasis or diabetic neuropathy in a patient comprising administration of an effective amount of the antagonist of claim 10.

16. A method for the treatment of solid tumors in a patient comprising administration of an effective amount of the antagonist of claim 10.

17. The method of claim 16, wherein tumor angiogenesis is inhibited.

18. A method for inhibition of endothelialization in a patient comprising administration of an effective amount of the antagonist of claim 10.

* * * * *

SEQUENCE LISTING

<160> NUMBER OF SEQ ID NOS: 9

<210> SEQ ID NO 1
<211> LENGTH: 1525
<212> TYPE: DNA
<213> ORGANISM: Homo sapiens
<220> FEATURE:
<221> NAME/KEY: CDS
<222> LOCATION: (71)..(1120)
<220> FEATURE:
<221> NAME/KEY: sig_peptide
<222> LOCATION: (71)..(142)
<220> FEATURE:
<221> NAME/KEY: mat_peptide
<222> LOCATION: (143)..(1120)

<400> SEQUENCE: 1
cgaggccacg gcttatgcaa gcaaagatct ggaggagcag ttacggtctg tgtccagtgt        60
agatgaactc atg act gta ctc tac cca gaa tat tgg aaa atg tac aag          109
              Met Thr Val Leu Tyr Pro Glu Tyr Trp Lys Met Tyr Lys
                  -20                                     -15

|   |   |
|---|---|
| tgt cag cta agg aaa gga ggc tgg caa cat aac aga gaa cag gcc aac<br>Cys Gln Leu Arg Lys Gly Gly Trp Gln His Asn Arg Glu Gln Ala Asn<br>    -10              -5                     -1  1                   5 | 157 |
| ctc aac tca agg aca gaa gag act ata aaa ttt gct gca gca cat tat<br>Leu Asn Ser Arg Thr Glu Glu Thr Ile Lys Phe Ala Ala Ala His Tyr<br>             10                           15                      20 | 205 |
| aat aca gag atc ttg aaa agt att gat aat gag tgg aga aag act caa<br>Asn Thr Glu Ile Leu Lys Ser Ile Asp Asn Glu Trp Arg Lys Thr Gln<br>            25                       30                       35 | 253 |
| tgc atg cca cgg gag gtg tgt ata gat gtg ggg aag gag ttt gga gtc<br>Cys Met Pro Arg Glu Val Cys Ile Asp Val Gly Lys Glu Phe Gly Val<br>            40                     45                    50 | 301 |
| gcg aca aac acc ttc ttt aaa cct cca tgt gtg tcc gtc tac aga tgt<br>Ala Thr Asn Thr Phe Phe Lys Pro Pro Cys Val Ser Val Tyr Arg Cys<br>      55                      60                    65 | 349 |
| ggg ggt tgc tgc aat agt gag ggg ctg cag tgc atg aac acc agc acg<br>Gly Gly Cys Cys Asn Ser Glu Gly Leu Gln Cys Met Asn Thr Ser Thr<br>    70                  75                    80                  85 | 397 |
| agc tac ctc agc aag acg tta ttt gaa att aca gtg cct ctc tct caa<br>Ser Tyr Leu Ser Lys Thr Leu Phe Glu Ile Thr Val Pro Leu Ser Gln<br>              90                     95                    100 | 445 |
| ggc ccc aaa cca gta aca atc agt ttt gcc aat cac act tcc tgc cga<br>Gly Pro Lys Pro Val Thr Ile Ser Phe Ala Asn His Thr Ser Cys Arg<br>           105                     110                  115 | 493 |
| tgc atg tct aaa ctg gat gtt tac aga caa gtt cat tcc att att aga<br>Cys Met Ser Lys Leu Asp Val Tyr Arg Gln Val His Ser Ile Ile Arg<br>           120                     125                  130 | 541 |
| cgt tcc ctg cca gca aca cta cca cag tgt cag gca gcg aac aag acc<br>Arg Ser Leu Pro Ala Thr Leu Pro Gln Cys Gln Ala Ala Asn Lys Thr<br>    135                       140                    145 | 589 |
| tgc ccc acc aat tac atg tgg aat aat cac atc tgc aga tgc ctg gct<br>Cys Pro Thr Asn Tyr Met Trp Asn Asn His Ile Cys Arg Cys Leu Ala<br>150                    155                    160                  165 | 637 |
| cag gaa gat ttt atg ttt tcc tcg gat gct gga gat gac tca aca gat<br>Gln Glu Asp Phe Met Phe Ser Ser Asp Ala Gly Asp Asp Ser Thr Asp<br>                 170                     175                  180 | 685 |
| gga ttc cat gac atc tgt gga cca aac aag gag ctg gat gaa gag acc<br>Gly Phe His Asp Ile Cys Gly Pro Asn Lys Glu Leu Asp Glu Glu Thr<br>           185                     190                  195 | 733 |
| tgt cag tgt gtc tgc aga gcg ggg ctt cgg cct gcc agc tgt gga ccc<br>Cys Gln Cys Val Cys Arg Ala Gly Leu Arg Pro Ala Ser Cys Gly Pro<br>           200                     205                  210 | 781 |
| cac aaa gaa cta gac aga aac tca tgc cag tgt gtc tgt aaa aac aaa<br>His Lys Glu Leu Asp Arg Asn Ser Cys Gln Cys Val Cys Lys Asn Lys<br>215                    220                    225 | 829 |
| ctc ttc ccc agc caa tgt ggg gcc aac cga gaa ttt gat gaa aac aca<br>Leu Phe Pro Ser Gln Cys Gly Ala Asn Arg Glu Phe Asp Glu Asn Thr<br>230                    235                    240                  245 | 877 |
| tgc cag tgt gta tgt aaa aga acc tgc ccc aga aat caa ccc cta aat<br>Cys Gln Cys Val Cys Lys Arg Thr Cys Pro Arg Asn Gln Pro Leu Asn<br>               250                     255                  260 | 925 |
| cct gga aaa tgt gcc tgt gaa tgt aca gaa agt cca cag aaa tgc ttg<br>Pro Gly Lys Cys Ala Cys Glu Cys Thr Glu Ser Pro Gln Lys Cys Leu<br>           265                     270                  275 | 973 |
| tta aaa gga aag aag ttc cac cac caa aca tgc agc tgt tac aga cgg<br>Leu Lys Gly Lys Lys Phe His His Gln Thr Cys Ser Cys Tyr Arg Arg<br>           280                     285                  290 | 1021 |
| cca tgt acg aac cgc cag aag gct tgt gag cca gga ttt tca tat agt<br>Pro Cys Thr Asn Arg Gln Lys Ala Cys Glu Pro Gly Phe Ser Tyr Ser<br>    295                     300                    305 | 1069 |

-continued

```
gaa gaa gtg tgt cgt tgt gtc cct tca tat tgg caa aga cca caa atg      1117
Glu Glu Val Cys Arg Cys Val Pro Ser Tyr Trp Gln Arg Pro Gln Met
310             315                 320                 325 agc taagattgta ctgttttcca gttcatcgat tttctattat ggaaaactgt            1170
Ser gttgccacag tagaactgtc tgtgaacaga gagaccttg tgggtccatg ctaacaaga       1230 caaaagtctg tctttcctga accatgtgga taactttaca gaaatggact ggagctcatc    1290 tgcaaaggc ctcttgtaaa gactggtttt ctgccaatga ccaaacagcc aagattttcc     1350
tcttgtgatt tctttaaaag aatgactata taatttattt ccactaaaaa tattgtttct   1410
gcattcattt ttatagcaac aacaattggt aaaactcact gtgatcaata tttttatatc   1470
atgcaaaata tgtttaaaat aaaatgaaaa ttgtattata aaaaaaaaaa aaaaa          1525
```

<210> SEQ ID NO 2
<211> LENGTH: 350
<212> TYPE: PRT
<213> ORGANISM: Homo sapiens

<400> SEQUENCE: 2

```
Met Thr Val Leu Tyr Pro Glu Tyr Trp Lys Met Tyr Lys Cys Gln Leu
            -20                 -15                 -10

Arg Lys Gly Gly Trp Gln His Asn Arg Glu Gln Ala Asn Leu Asn Ser
         -5                 -1   1               5

Arg Thr Glu Glu Thr Ile Lys Phe Ala Ala His Tyr Asn Thr Glu
     10                  15                  20

Ile Leu Lys Ser Ile Asp Asn Glu Trp Arg Lys Thr Gln Cys Met Pro
 25                  30                  35                  40

Arg Glu Val Cys Ile Asp Val Gly Lys Glu Phe Gly Val Ala Thr Asn
                 45                  50                  55

Thr Phe Phe Lys Pro Pro Cys Val Ser Val Tyr Arg Cys Gly Gly Cys
             60                  65                  70

Cys Asn Ser Glu Gly Leu Gln Cys Met Asn Thr Ser Thr Ser Tyr Leu
         75                  80                  85

Ser Lys Thr Leu Phe Glu Ile Thr Val Pro Leu Ser Gln Gly Pro Lys
     90                  95                  100

Pro Val Thr Ile Ser Phe Ala Asn His Thr Ser Cys Arg Cys Met Ser
105                  110                  115                  120

Lys Leu Asp Val Tyr Arg Gln Val His Ser Ile Ile Arg Arg Ser Leu
                 125                  130                  135

Pro Ala Thr Leu Pro Gln Cys Gln Ala Ala Asn Lys Thr Cys Pro Thr
             140                  145                  150

Asn Tyr Met Trp Asn Asn His Ile Cys Arg Cys Leu Ala Gln Glu Asp
         155                  160                  165

Phe Met Phe Ser Ser Asp Ala Gly Asp Asp Ser Thr Asp Gly Phe His
     170                  175                  180

Asp Ile Cys Gly Pro Asn Lys Glu Leu Asp Glu Glu Thr Cys Gln Cys
185                  190                  195                  200

Val Cys Arg Ala Gly Leu Arg Pro Ala Ser Cys Gly Pro His Lys Glu
                 205                  210                  215

Leu Asp Arg Asn Ser Cys Gln Cys Val Cys Lys Asn Lys Leu Phe Pro
             220                  225                  230

Ser Gln Cys Gly Ala Asn Arg Glu Phe Asp Glu Asn Thr Cys Gln Cys
         235                  240                  245
```

```
Val Cys Lys Arg Thr Cys Pro Arg Asn Gln Pro Leu Asn Pro Gly Lys
    250                 255                 260

Cys Ala Cys Glu Cys Thr Glu Ser Pro Gln Lys Cys Leu Leu Lys Gly
265                 270                 275                 280

Lys Lys Phe His His Gln Thr Cys Ser Cys Tyr Arg Arg Pro Cys Thr
                285                 290                 295

Asn Arg Gln Lys Ala Cys Glu Pro Gly Phe Ser Tyr Ser Glu Glu Val
            300                 305                 310

Cys Arg Cys Val Pro Ser Tyr Trp Gln Arg Pro Gln Met Ser
            315                 320                 325

<210> SEQ ID NO 3
<211> LENGTH: 14
<212> TYPE: PRT
<213> ORGANISM: Homo sapiens
<220> FEATURE:
<221> NAME/KEY: SITE
<222> LOCATION: (2)
<223> OTHER INFORMATION: Xaa equals any amino acid
<220> FEATURE:
<221> NAME/KEY: SITE
<222> LOCATION: (5)..(7)
<223> OTHER INFORMATION: Xaa equals any amino acid
<220> FEATURE:
<221> NAME/KEY: SITE
<222> LOCATION: (10)
<223> OTHER INFORMATION: Xaa equals any amino acid

<400> SEQUENCE: 3

Pro Xaa Cys Val Xaa Xaa Xaa Arg Cys Xaa Gly Cys Cys Asn
  1               5                  10

<210> SEQ ID NO 4
<211> LENGTH: 18
<212> TYPE: DNA
<213> ORGANISM: Homo sapiens

<400> SEQUENCE: 4
atgcttccgg ctcgtatg                                                   18

<210> SEQ ID NO 5
<211> LENGTH: 19
<212> TYPE: DNA
<213> ORGANISM: Homo sapiens

<400> SEQUENCE: 5
gggttttccc agtcacgac                                                  19

<210> SEQ ID NO 6
<211> LENGTH: 21
<212> TYPE: DNA
<213> ORGANISM: Homo sapiens

<400> SEQUENCE: 6
ccacatggtt caggaaagac a                                               21

<210> SEQ ID NO 7
<211> LENGTH: 196
<212> TYPE: PRT
<213> ORGANISM: Homo sapiens

<400> SEQUENCE: 7

Met Arg Thr Leu Ala Cys Leu Leu Leu Gly Cys Gly Tyr Leu Ala
  1               5                  10                  15
```

```
His Val Leu Ala Glu Ala Glu Ile Pro Arg Glu Val Ile Glu Arg
            20                  25                  30

Leu Ala Arg Ser Gln Ile His Ser Ile Arg Asp Leu Gln Arg Leu Leu
        35                  40                  45

Glu Ile Asp Ser Val Gly Ser Glu Asp Ser Leu Asp Thr Ser Leu Arg
 50                  55                  60

Ala His Gly Val His Ala Thr Lys His Val Pro Glu Lys Arg Pro Leu
 65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Asp Val Arg
        195

<210> SEQ ID NO 8
<211> LENGTH: 241
<212> TYPE: PRT
<213> ORGANISM: Homo sapiens

<400> SEQUENCE: 8

Met Asn Arg Cys Trp Ala Leu Phe Leu Ser Leu Cys Cys Tyr Leu Arg
 1               5                  10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
 50                  55                  60

Thr Arg Ser His Ser Gly Gly Glu Leu Glu Ser Leu Ala Arg Gly Arg
 65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190
```

-continued

```
Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala

<210> SEQ ID NO 9
<211> LENGTH: 232
<212> TYPE: PRT
<213> ORGANISM: Homo sapiens

<400> SEQUENCE: 9

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Lys Asn Glu Arg Thr
210                 215                 220

Cys Arg Cys Asp Lys Pro Arg Arg
225                 230
```